United States Patent
Becher et al.

(10) Patent No.: US 10,499,646 B2
(45) Date of Patent: Dec. 10, 2019

(54) HERBICIDAL COMPOSITIONS CONTAINING N-PHOSPHONOMETHYL GLYCINE AND AN AUXIN HERBICIDE

(71) Applicant: Monsanto Technology LLC, St. Louis, MO (US)

(72) Inventors: David Z. Becher, St. Louis, MO (US); Henry E. Agbaje, St. Louis, MO (US); Jeffrey N. Travers, Chesterfield, MO (US); Ronald J. Brinker, Ellisville, MO (US); Xiaodong C. Xu, Valley Park, MO (US); Timothy S. Ottens, Stanton, MO (US)

(73) Assignee: Monsanto Technology LLC, St. Louis, MO (US)

(*) Notice: Subject to any disclaimer, the term of this patent is extended or adjusted under 35 U.S.C. 154(b) by 1226 days.

(21) Appl. No.: 14/273,025

(22) Filed: May 8, 2014

(65) Prior Publication Data
US 2014/0364313 A1  Dec. 11, 2014

Related U.S. Application Data

(63) Continuation of application No. 12/802,395, filed on Jun. 4, 2010, now abandoned, which is a continuation of application No. 11/077,279, filed on Mar. 10, 2005, now abandoned.

(60) Provisional application No. 60/552,065, filed on Mar. 10, 2004.

(51) Int. Cl.
| *A01N 57/20* | (2006.01) |
| *A01N 25/30* | (2006.01) |
| *A01N 37/40* | (2006.01) |
| *A01N 39/04* | (2006.01) |
| *A01N 37/38* | (2006.01) |

(52) U.S. Cl.
CPC ............ *A01N 57/20* (2013.01); *A01N 25/30* (2013.01); *A01N 37/38* (2013.01); *A01N 37/40* (2013.01)

(58) Field of Classification Search
CPC combination set(s) only.
See application file for complete search history.

(56) References Cited

U.S. PATENT DOCUMENTS

| 2,505,059 A | 4/1950 | Moore |
| 3,013,054 A | 12/1961 | Richter |
| 3,276,856 A | 10/1966 | Esposito |
| 3,594,151 A | 7/1971 | Sprayberry et al. |
| 3,600,407 A | 8/1971 | Levin et al. |
| 3,713,404 A | 1/1973 | Lavo et al. |
| 3,751,239 A | 8/1973 | McNulty et al. |
| 3,799,758 A | 3/1974 | Franz |
| 3,852,340 A | 12/1974 | Reck et al. |
| 3,870,732 A | 3/1975 | Hokama |
| 3,910,974 A | 10/1975 | Hokama |
| 3,923,849 A | 12/1975 | Hokama |
| 4,022,610 A | 5/1977 | Hokama |
| 4,405,531 A | 9/1983 | Franz |
| 4,445,927 A | 5/1984 | Gimesi et al. |
| 4,534,783 A | 8/1985 | Beestman |
| 4,546,196 A | 10/1985 | Luteri et al. |
| H0000303 H | 7/1987 | Malik et al. |
| 4,692,184 A | 9/1987 | Lee |
| 4,729,781 A | 3/1988 | Williams |
| 4,936,900 A | 6/1990 | Hyson |
| 4,936,901 A | 6/1990 | Surgant, Sr. et al. |
| 5,004,863 A | 4/1991 | Umbeck |
| 5,015,580 A | 5/1991 | Christou et al. |
| 5,035,738 A | 7/1991 | Burns et al. |
| 5,152,823 A | 10/1992 | Albrecht et al. |
| 5,159,135 A | 10/1992 | Umbeck |
| 5,175,353 A | 12/1992 | Jones et al. |
| 5,221,319 A | 6/1993 | Van Haften et al. |
| 5,229,354 A | 7/1993 | Narayanan et al. |
| 5,229,355 A | 7/1993 | Chaudhuri et al. |
| 5,231,070 A | 7/1993 | Narayanan et al. |
| 5,250,500 A | 10/1993 | Jones et al. |
| 5,266,553 A | 11/1993 | Champion et al. |
| 5,283,228 A | 2/1994 | Narayanan et al. |
| 5,317,003 A | 5/1994 | Kassebaum et al. |
| 5,384,253 A | 1/1995 | Krzyzek et al. |
| 5,416,011 A | 5/1995 | Hinchee et al. |

(Continued)

FOREIGN PATENT DOCUMENTS

| AU | 10073/92 B | 10/1992 |
| AU | 2005221166 B2 | 9/2005 |

(Continued)

OTHER PUBLICATIONS

Wicks, Gail A. et al., "Influence of Small Grain Crops on Weeds and Ecofallow Corn (*Zea mays*)", Weed Science, 1995, pp. 128-133, vol. 43, Issue 1.

(Continued)

*Primary Examiner* — John Pak
(74) *Attorney, Agent, or Firm* — Stinson LLP; Erin C. Robert

(57) ABSTRACT

Herbicidal compositions are provided which cause rapid symptomology while delivering long term control of regrowth of plants. The herbicidal concentrate compositions comprise N-phosphonomethylglycine or a herbicidal derivative thereof, an auxin herbicide or a herbicidal derivative thereof, and at least one surfactant. Also provided is a method for killing or controlling the growth of certain plants by contacting the foliage of the plants with the diluted concentrate composition.

22 Claims, No Drawings

(56) References Cited

U.S. PATENT DOCUMENTS

| | | |
|---|---|---|
| 5,434,783 A | 7/1995 | Pal et al. |
| 5,436,223 A | 7/1995 | Mulqueen et al. |
| 5,463,174 A | 10/1995 | Moloney et al. |
| 5,508,184 A | 4/1996 | Negrutiu et al. |
| 5,518,908 A | 5/1996 | Corbin et al. |
| 5,538,880 A | 6/1996 | Lundquist et al. |
| 5,550,318 A | 8/1996 | Adams et al. |
| 5,565,409 A | 10/1996 | Sato et al. |
| 5,569,834 A | 10/1996 | Hinchee et al. |
| 5,591,616 A | 1/1997 | Hiei et al. |
| 5,631,152 A | 5/1997 | Fry et al. |
| 5,668,085 A | 9/1997 | Forbes et al. |
| 5,670,454 A | 9/1997 | Grossmann et al. |
| 5,703,015 A | 12/1997 | Berger et al. |
| 5,733,848 A | 3/1998 | Luteri |
| 5,750,468 A | 5/1998 | Wright et al. |
| 5,824,877 A | 10/1998 | Hinchee et al. |
| 5,834,006 A | 11/1998 | Smith et al. |
| 5,877,112 A | 3/1999 | Roberts |
| 5,883,046 A | 3/1999 | Luteri |
| 5,883,048 A | 3/1999 | Morre et al. |
| 5,965,487 A | 10/1999 | Flahive |
| 5,981,840 A | 11/1999 | Zhao et al. |
| 5,998,332 A | 12/1999 | Sato et al. |
| 6,030,923 A | 2/2000 | Okano et al. |
| 6,060,432 A | 5/2000 | Adams et al. |
| 6,063,733 A | 5/2000 | Berger et al. |
| 6,121,199 A | 9/2000 | Berger et al. |
| 6,133,199 A | 10/2000 | Soula et al. |
| 6,160,208 A | 12/2000 | Lundquist et al. |
| 6,177,414 B1 | 1/2001 | Tomalia et al. |
| 6,228,807 B1 | 5/2001 | Kuchikata et al. |
| 6,245,713 B1 | 6/2001 | Brinker et al. |
| 6,277,788 B1 | 8/2001 | Wright |
| 6,300,323 B1 | 10/2001 | Haga et al. |
| 6,337,078 B1 | 1/2002 | Levy |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,410,783 B1 | 6/2002 | Peterson et al. |
| 6,417,140 B1 | 7/2002 | Lee et al. |
| 6,436,874 B1 | 8/2002 | Kuah et al. |
| 6,455,473 B2 | 9/2002 | Wright |
| RE37,866 E | 10/2002 | Wright et al. |
| 6,500,783 B1 | 12/2002 | Bryson et al. |
| 6,569,809 B1 | 5/2003 | Sato et al. |
| 6,579,831 B1 | 6/2003 | Harwell |
| 6,586,367 B2 | 7/2003 | Lee et al. |
| 6,677,276 B1 | 1/2004 | Hacker et al. |
| 6,713,433 B2 | 3/2004 | Jimoh |
| 6,723,681 B2 | 4/2004 | Hacker et al. |
| 6,774,087 B1 | 8/2004 | Nakayama et al. |
| 6,906,004 B2 | 6/2005 | Parrish et al. |
| 6,939,555 B2 | 9/2005 | Volgas et al. |
| 7,135,437 B2 | 11/2006 | Pallas et al. |
| 7,223,718 B2 | 5/2007 | Smiley |
| 7,431,845 B2 | 10/2008 | Manek et al. |
| 7,695,541 B1 | 4/2010 | Frizzell et al. |
| 2002/0107149 A1 | 8/2002 | Volgas et al. |
| 2002/0123430 A1 | 9/2002 | Xu et al. |
| 2002/0155953 A1 | 10/2002 | Brigance |
| 2003/0004063 A1 | 1/2003 | Jimoh |
| 2003/0022791 A1 | 1/2003 | Asrar et al. |
| 2003/0087764 A1 | 5/2003 | Pallas |
| 2003/0104943 A1 | 6/2003 | Lennon et al. |
| 2004/0077499 A1 | 4/2004 | Graham et al. |
| 2004/0138176 A1 | 7/2004 | Miles |
| 2005/0026780 A1 | 2/2005 | Parrish |
| 2006/0019828 A1 | 1/2006 | Becher et al. |
| 2006/0040828 A1 | 2/2006 | Mao et al. |
| 2006/0270556 A1 | 11/2006 | Wright et al. |
| 2007/0093462 A1 | 4/2007 | Rogers et al. |
| 2007/0149409 A1 | 6/2007 | Burnet et al. |
| 2007/0184980 A1 | 8/2007 | Roberts et al. |
| 2007/0259789 A1 | 11/2007 | Huchet et al. |
| 2008/0119361 A1 | 5/2008 | Feng et al. |
| 2008/0153706 A1 | 6/2008 | Frisch et al. |
| 2008/0182773 A1 | 7/2008 | Gauweiler et al. |
| 2008/0207452 A1 | 8/2008 | Kramer et al. |
| 2008/0207453 A1 | 8/2008 | Kramer et al. |
| 2009/0041813 A1 | 2/2009 | Bouillo et al. |
| 2009/0062127 A1 | 3/2009 | Liu |
| 2009/0093366 A1 | 4/2009 | Wright et al. |
| 2009/0170702 A1 | 7/2009 | Yoshii et al. |
| 2010/0113274 A1 | 5/2010 | Hemminghaus et al. |
| 2010/0273654 A1 | 10/2010 | Li et al. |
| 2010/0331182 A1 | 12/2010 | Zhang et al. |
| 2011/0019652 A1 | 1/2011 | Atwal |
| 2011/0034332 A1 | 2/2011 | Becher et al. |
| 2011/0275517 A1 | 11/2011 | Satchivi et al. |
| 2012/0142532 A1 | 6/2012 | Wright et al. |
| 2012/0184434 A1 | 7/2012 | Xu et al. |
| 2014/0171321 A1 | 6/2014 | Wright et al. |
| 2014/0249026 A1 | 9/2014 | Hemminghaus et al. |
| 2014/0309114 A1 | 10/2014 | Zhang et al. |
| 2015/0164082 A1 | 6/2015 | MacInnes et al. |
| 2016/0366878 A1 | 12/2016 | Wright et al. |

FOREIGN PATENT DOCUMENTS

| | | |
|---|---|---|
| AU | 2010202620 A1 | 7/2010 |
| CA | 1293974 C | 1/1992 |
| CA | 2340240 A1 | 2/2000 |
| CA | 2729738 A1 | 1/2010 |
| CN | 1513326 A | 7/2004 |
| DE | 4030687 A1 | 5/1991 |
| DE | 19836660 | 2/2000 |
| DE | 19836684 | 2/2000 |
| DE | 19836700 | 2/2000 |
| DE | 19836737 | 2/2000 |
| EP | 0375624 A1 | 6/1990 |
| EP | 0290416 | 6/1993 |
| EP | 0360441 | 4/1994 |
| EP | 0808569 D4 | 11/1997 |
| EP | 1023832 A1 | 8/2000 |
| GB | 851008 A | 10/1960 |
| GB | 1262123 A | 2/1972 |
| GB | 2267825 A | 12/1993 |
| RU | 2208930 C1 | 7/2003 |
| RU | 2366176 C2 | 9/2009 |
| RU | 2384064 C1 | 3/2010 |
| RU | 2395203 C1 | 7/2010 |
| RU | 2408188 C1 | 1/2011 |
| WO | 9212637 A1 | 9/1992 |
| WO | 95/16351 | 6/1995 |
| WO | 97/31535 | 9/1997 |
| WO | 99/00013 A2 | 1/1999 |
| WO | 9905914 A1 | 2/1999 |
| WO | 00/08936 | 2/2000 |
| WO | 0005951 A1 | 2/2000 |
| WO | 0005952 A1 | 2/2000 |
| WO | 00/15037 | 3/2000 |
| WO | WO 00/30451 * | 5/2000 |
| WO | 0030452 A1 | 6/2000 |
| WO | 00/64257 A1 | 11/2000 |
| WO | 00/67571 | 11/2000 |
| WO | 2001/17358 | 3/2001 |
| WO | 01/35740 A2 | 5/2001 |
| WO | 2001/89302 | 11/2001 |
| WO | 02/21924 A2 | 3/2002 |
| WO | 02/096199 | 12/2002 |
| WO | 02/102153 A2 | 12/2002 |
| WO | 03/013241 | 2/2003 |
| WO | 2003024218 A1 | 3/2003 |
| WO | 2004/093546 A1 | 11/2004 |
| WO | 2005087007 A1 | 9/2005 |
| WO | 2005115144 A1 | 12/2005 |
| WO | 2007110355 A2 | 10/2006 |
| WO | 2008030749 A2 | 3/2008 |
| WO | 2008101818 A2 | 8/2008 |
| WO | 2008106118 A3 | 9/2008 |
| WO | 2009060026 A2 | 5/2009 |
| WO | 2010046422 A2 | 4/2010 |
| WO | 2010071936 A1 | 7/2010 |

(56) References Cited

FOREIGN PATENT DOCUMENTS

| WO | 2010102102 A1 | 9/2010 |
|---|---|---|
| WO | 2010147966 A1 | 12/2010 |
| WO | 2011026800 A2 | 3/2011 |
| WO | 2012040785 A1 | 4/2012 |
| WO | 2012104237 A2 | 8/2012 |
| WO | 2012163824 A1 | 12/2012 |
| WO | 2013063357 A2 | 2/2013 |
| WO | 2013184622 A2 | 12/2013 |
| WO | 2014134235 A1 | 9/2014 |

OTHER PUBLICATIONS

Wicks, Gail A. et al., "Survey of Winter Wheat (*Triticum aestivum*) Stubble Fields Sprayed with Herbicides After Harvest in 1986", Weed Technology, 1989, pp. 244-254, vol. 3, Issue 2.
Wiese, Allen F. et al., "Downy Brame (*Bromus tectorum*), Jointed Goatgrass (*Aegilops cylindrica*) and Horseweed (*Conyza canadensis*) Control in Fallow", Weed Technology, 1995, pp. 249-254, vol. 9, Issue 2.
Wiese, Allen F. et al., "Economic evaluation of field bindweed (*Convolvulus arvensis*) control", Weed Science, 1997, pp. 288-295, vol. 45.
Wiese, Allen F. et al., "Economic Evaluation of Field Bindweed (*Convolvulus arvensis*) Control in a Winter Wheat-Fallow Rotation", Weed Science, 1996, pp. 622-628, vol. 44, Issue 3.
Wilson, John S. et al., "Combinations of Nonselective Herbicides for Difficult to Control Weeds in No-Till Corn, Zea Mays, and Soybeans, Glycine max", Weed Science, 1988, pp. 648-652, vol. 36, Issue 5.
Woznica, Zenon, "Effect of Water Quality and Adjuvants on Phytotoxicity of Glyphosate", Roczniki nauk rolniczych. Seria E: Ochrona roslin, 1992, pp. 97-101, vol. 22.
Wyrill, J.B., et al., "Glyphosate Toxicity to Common Milkweed and Hemp Dogbane as Influenced by Surfactants," 1977, Weed Science, 25/3:275-287.
Yarborough, David E. et al., "Barrenberry aronia melanocarpa (Michx.) Eli, Control in Native Lowbush Blueberry Vaccinium angustifolium Ait. Fields through Selective Applications of 2,4-D (2,4-Dichlorophenoxyacetic Acid) and Glyphosate [N-(Phosphonomethyl) Glycene]", HortScience, 1978, pp. 353-354, vol. 13, Issue 3, Section 2, American Society for Horticultural Science.
Application for Amended Product Label, Banvel Herbicide (BASF Corporation), EPA Reg. No. 7969-131, Jul. 18, 2001, 19 pages.
Application for Amended Product Label, Clarity Herbicide (BASF Corporation), EPA Reg. No. 7969-137, Jul. 19, 2000, 20 pages.
Label Revisions, Tordon 22K Weed Killer (Dow AgroSciences LLC), EPA Reg. No. 62719-6, Dec. 30, 1998, 31 pages.
Label Revisions, Fallow Master Herbicide (Monsanto Company), EPA Reg. No. 524-390, Jul. 14, 1997, 17 pages.
Label Amendment, Banval Herbicide (BASF Corporation), EPA Reg. No. 55947-38, May 17, 1994, 56 pages.
EPA Notice of Pesticide Registration, MON 78270 Herbicide (Monsanto Company), EPA Reg. No. 524-437, Apr. 11, 2002, 120 pages.
EPA Notice of Pesticide Registration, Roundup VM Herbicide (Monsanto Company), EPA Reg. No. 424-544, Oct. 10, 2002, 123 pages.
Notification of Alternate Brand Name, RT Master I Herbicide (Monsanto Company), EPA Reg. No. 524-539, Jul. 9, 2003, 32 pages.
Supplemental Product Label, Roundup WeatherMAX Herbice (Monsanto Company), EPA Reg. No. 524-537, Accepted Feb. 6, 2003, 2 pages.
Supplemental Product Label, Roundup Original Max Herbicide (Monsanto Company), EPA Reg. No. 524-539, Accepted Oct. 30, 2003, 6 pages.
Draft Product Label, Roundup PowerMax Herbicide (Monsanto Company), Label No. 55687/1201, N.R.A. Approved Text Oct. 10, 2003, 13 page.

Product Label, RT Master Herbicide (Monsanto Company), EPA Reg. No. 524-LGR, Accepted Jun. 29, 2001, 28 pages.
Product Label, Amicide Selective Herbicide (Nufarm Australia Limited), NRA Approval No. 52904/0800, 15 pages.
Product Label, Buttress Selective Herbicide (Nufarm Limited), NRA Approval No. 46043/02, Dec. 1997, 8 pages.
Product Label, Conqueror Herbicide (Nufarm Australia Limited), NRA Approval No. 57783/0703, 6 pages.
Product Label, Lantana DP-600 Herbicide (Nurfarm Australia Limited), NRA Approval No. 41494/0299, 1 page.
Product Label, Kamba 500 Selective Herbicide (Nufarm Australia Limited), NRA File No. 51080/0902, 6 pages.
Product Label, L.V.E. MCPA Low-Volatile Ester Herbicide (Nufarm Australia Limited), NRA Approval No. 31521/0603, 2 pages.
Product Label, LV Estercide 600 Herbicide (Nufarm Australia Limited), NRA File No. 42229/0902, 5 pages.
Product Label, Paramount Herbicide (BASF Corporation), EPA Ref. No. 7969-113, Jul. 30, 2003, 8 pages.
Product Label, Starmas Herbicide (Mastra Industries SDN BHD), Oct. 15, 2003, 9 pages.
Product Label, Surpass 300 (Nufarm Australia Limited), NRA Approval No. 52999/0902, 7 pages.
Product Label, Tillmaster Herbicide (Nufarm Australia Limited), NRA Approval No. 32162/1097, 1 page.
Product Label, Touchdown Hi Tech Herbicide (Syngenta Crop Protection), NRA Approval No. 54617/0502, 12 pages.
Fallow Master (Monsanto Company) Material Safety Data Sheet, EPA Reg. No. 524-506, Effective Jan. 31, 2003, 11 pages.
Statutory Declaration of Phillip Maxwell Hay, dated Jul. 13, 2012, filed in Opposition Proceeding in Australian Patent Application 2005221166, 91 pages.
Communication of Notices of Opposition, dated Jun. 4, 2012, issued in European Patent Application No. 05725288.4, 1 page.
Communication of Notice of Opposition, dated May 4, 2012, issued in European Patent Application No. 05725288.4, 18 pages.
Fallow Master Herbicide Label, EPA Reg. No. 524-507, copyright 2000, 5 pages.
Derivative, Merriam-Webster's Collegiate Dictionary, 1996, Tenth Edition, 3 pages.
International Search Report, PCT/US2005/008029, dated Aug. 31, 2005, 3 pages.
Abdul Salam, M. et al., "Efficacy of Chemical Weed Control in Cashew Plantations", Journal of Plantation Crops, Jun. 1993, pp. 54-56, vol. 21, Issue 1.
Al-Khatib, Kassim et al., "Sweet Cherry (*Prunus avium*) Response to Simulated Drift from Selected Herbicides", Weed Technology, 1992, pp. 975-979, vol. 6, Issue 4.
Alm, David M. et al., "Weed Suppression for Weed Management in Corn (*Zea mays*) and Soybean (*Glycine max*) Production Systems", Weed Technology, 2000, pp. 713-717, vol. 14, Issue 4.
Beck, K. George et al., "Jointed Goatgrass (*Aegilops cylindrica*) and Downy Brome (*Bromus tectorum*) Control in Perennial Grasses", Weed Technology, 1995, pp. 255-259, vol. 9, Issue 2.
Blackshaw, Robert E., "Control of Downy Brome (*Bromus tectorum*) in Conservation Fallow Systems", Weed Technology, 1991, pp. 557-562, vol. 5, Issue 3.
Combellack, Joseph H., et al., "The Influence of Adjuvants on the Performance of a Glyphosate/2,4-D Mixture", Adjuvants for Agrichemicals, 1992, pp. 303-310, Chapter 29.
Cramer, Gary L. et al., "Control of Common Milkweed (*Asclepias syriaca*)", Weed Science, 1981, pp. 636-640, vol. 29, Issue 6.
Culpepper, A.S., et al., "Morningglory (*Ipomoea* spp.) and Large Crabgrass (*Gigitaria sanguinalis*) Control with Glyphosate and 2,4-Db Mixtures in Glyphosate-Resistant Soybean (*Glycine max*)," 2001, Weed Tech, 15:56-61.
Currie, Randall S. et al., "Effects of Herbicides and Application Timing on Woollyleaf Bursage (*Ambrosia grayi*)", Weed Technology, 2000, pp. 188-190, vol. 14, Issue 1.
De Barreda, D.G. et al., "Evaluation of Glyphosate for Weed Control in Citrus Orchards of Spain", Proceedings of the International Society of Citriculture, 1981, pp. 487-489, vol. 2, International Society of Citriculture, Tokyo, Japan.

(56) References Cited

OTHER PUBLICATIONS

Enloe, Stephen F. et al., "Use of Quinclorac Plus 2,4-D for Controlling Field Bindweed (*Convolvulus arvensis*) in Fallow", Weed Technology, 1999, pp. 731-736, vol. 13, Issue 4.
Faiz, M.A. Ahmad, "Effects of Herbicide Mixtures, Surfactants and Spray Volumes on the Control of *Imperata cylindrica* (L.) Raeuschel", Journal of Rubber Research, 1998, pp. 179-189, vol. 1, Issue 3.
Figueroa, P.F., "First-Year Results of a Herbicide Screening Trial in a Newly Established Red Alder Plantation with 1+0 Bare-Root and Plug Seedling Stock", Proc. of Western Soc. of Weed Sci., 1988, pp. 108-124, vol. 41.
Flint, J.L. et al., "Antagonism of Glyphosate Toxicity to Johnsongrass (*Sorghum halepense*) by 2,4-D and Dicamba", Weed Science, 1989, pp. 700-705, vol. 37, Issue 5.
Flint, Jerry L. et al., "Effects of Glyphosate Combinations with 2,4-D or Dicamba on Field Bindweed (*Convolvulus arvensis*)", Weed Science, 1989, pp. 12-18, vol. 37, Issue 1.
Foloni, L.L., "Evaluation of Pre-Plant and Pre- and Post-Emergence Herbicides for No-Till Cotton in Cerrados Areas", The 1997 Brighton Crop Protection Conference—Weeds, 1997, pp. 863-868.
Franz, J.E., et al., "Glyphosate: A Unique Global Herbicide, Chapter 7, Glyphosate Herbicide Compositions, Additives, and Mixtures" 1997, ACS Monograph 189, pp. 187-231.
Gigax, Danny R. et al., "Field Bindweed Control with Fall-Applied Glyphosate and 2,4-D", Proceedings—North Central Weed Control Conference, 1978, pp. 153-158, vol. 33.
Glenn, Scott et al., "Canada Thistle (*Cirsium arvense*) Control in No-Tillage Corn (*Zea mays*)", Weed Technology, 1994, pp. 134-138, vol. 8.
Heap, I.M., "Herbicide Resistance—Australia vs. The Rest of the World," Thirteenth Australian Weeds Conference, Sep. 8-13, 2002, Perth, Western Australia, pp. 649-649.
Hoagland, R.E., "Interaction of Indoleacetic Acid and Glyphosate on Phenolic Metabolism in Soybeans", Pesticide Biochemistry and Physiology, 1990, pp. 68-75, vol. 36.
Kashin, A.A. et al., "Herbicide containing amine salts of N-phosphonomethylglycine and 2,4-dichlorophenoxyacetic acid", Chemical Abstracts, 1996, p. 473, vol. 124, No. 19, 253337n, American Chemical Society.
Landmaster® BW, Specimen Label, 1994, Monsanto Company.
Leys, A.R. et al., "Evaluation of herbicides for control of summer-growing weeds on fallows in south-eastern Australia", Australian Journal of Experimental Agriculture, 1990, pp. 271-279, vol. 30.
Lym, R.G. et al., "Effect of Glyphosate on Introduced and Native Grasses", Weed Technology, 1991, pp. 421-425, vol. 5, Issue 2.
Lym, R.G. et al., "Leafy Spurge (*Euphorbia esula*) Control, Forage Production, and Economic Return with Fall-Applied Herbicides", Weed Technology, 1994, pp. 824-829, vol. 8, Issue 4.
Miller, S.D., "Non-selective herbicides for weed control in fallow", Research Report—North Central Weed Control Conference, 1982, pp. 92 and 105, vol. 39, North Central Weed Control Conference, Champaign ,Illinois.
Milne, B., 1987 Results, Weed Research & Demonstration Unit, Orange, Department of Agriculture, Agricultural Research & Veterinary Center, New South Wales Government, 4 pages.
Milne, B., 1990 Results, Weed Research & Demonstration Unit, Orange, Department of Agriculture, Agricultural Research & Veterinary Center, New South Wales Government, 3 pages.
Milne, B., 1992 Results, Weed Research & Demonstration Unit, Orange, Department of Agriculture, Agricultural Research & Veterinary Center, New South Wales Government, 11 pages.
Moshier, L.J., "Response of Honeyvine Milkweed (*Ampelamus albidus*) to Herbicide Applications", Weed Science, 1980, pp. 722-724, vol. 28, Issue 6.
Moshier, Loren J. et al., "Honeyvine Milkweed (*Ampelarnus Albidus*) Response to Foliar Herbicides", Weed Science, 1986, pp. 730-734, vol. 34, Issue 5.
O'Sullivan, P.A., et al., "Interaction Between Glyphosate and Various Herbicides for Broadleaved Weed Control," 1980, Weed Research, 20:255-260.

O'Sullivan, P.A., et al., "Influence of Picloram on *Cirsium arvense* (L.) Scop. Control with Glyphosate," 1982, Weed Research, 22:251-256.
Ogg, Jr., A.G., et al., "Effects of Preplant Treatment Interval and Tillages on Herbicide Toxicity to Winter Wheat (*Triticum aestivum*)", Weed Technology, 1991, pp. 291-296, vol. 5, Issue 2.
Ramos, H.H., et al., "Efeitos da Qualidade da Água de Pulverização Sobre a Eficácia de Gerbicidas Aplicados em Pós-Emergência", Bragantia, Campinas, 1998, pp. 313-324, vol. 57, Issue 2.
Reynolds, D., et al., "Weed Science—Cutleaf Eveningprimrose Control with Preplant Burndown Herbicide Combinations in Cotton", The Journal of Cotton Science, 2000, pp. 124-128, vol. 4, Issue 2.
RT Master, Specimen Label, 2001, Monsanto Company.
Sarpe, N. et al., "Development of Various Strategies to Control Both Annual and Perennial Weed Species in Apple Orchards on Sandy Soils", Brighton Crop Protection Conference-Weeds, 1995, pp. 947-952.
Schultz, M.E. et al., "Absorption, Translocation, and Metabolism of 2,4-D and Glyphosate in Hemp Dogbane (*Apocynum cannabinum*)", Weed Science, 1980, pp. 13-20, vol. 28, Issue 1, Weed Science Society of America, Champaign, Illinois.
Sharma, Shiv D. et al., "Surfactants Increase Toxicity of Glyphosate and 2,4-D to Brazil Pusley", HortScience, 2001, pp. 726-728, vol. 36, Issue 4, American Society for Horticultural Science, Mt. Vernon, Virginia.
Smeda, Reid J. et al., "Biology and control of burcucumber", Weed Science, 2001, pp. 99-105, vol. 49.
Sprague, Ellis B., "Suppression of Brambles in Mechanized Strip Cuttings in Northern Maine", Proc. Ann. Mtg. Northeastern Weed Sci. Soc., 1979, pp. 47-49.
Thomas, P.E.L., "Chemical control of some broadleaved weeds which grow during winter in untilled maize lands", South African Journal of Plant and Soil, 1986, pp. 185-188, vol. 3, Issue 4.
Vencill, William K. (editor), Herbicide Handbook, Weed Science Society of America, 8th ed. (2002) at pp. 111-115 (2,4-D), pp. 116-118 (2,4-DB), pp. 133-135 (dichlorprop), pp. 276-278 (MCPA), pp. 281-283 (mecoprop) and pp. 345-348 (picloram).
Westra, Philip et al., "Field Bindweed (*Convolvulus arvensis*) Control with Various Herbicide Combinations", Weed Technology, 1992, pp. 949-955, vol. 6, Issue 4.
Whaley et al., "Effect of Fall Herbicide Treatments and Stage of Horsenettle (*Solanum carolinense*) Senescence on Control", Weed Technology, Apr. 2002, vol. 16, No. 2, pp. 301-308.
Wicks, Gail A. et al., "Control of Triazine-Resistant Kochia (*Kochia scoparia*) in Sorghum (*Sorghum bicolor*)", Weed Technology, 1994, pp. 748-753, vol. 8, Issue 4.
Wicks, Gail A. et al., "Effect of Herbicides Applied in Winter Wheat (*Triticum aestivum*) Stubble on Weed Management in Corn (*Zea mays*)", Weed Technology, 2000, pp. 705-712, vol. 14, Issue 4.
Wicks, Gail A. et al., "Effect of Rainfall on Glyphosate Plus 2,4-D Performance on Echinochloa crus-galli", Weed Science, 1995, pp. 666-670, vol. 43, Issue 4.
Yeiser, J.L., June, July and August Applications of Glyphosate Tank Mixes for Site Preparation, 1991, Proceedings Southern Weed Science Society, San Antonio, TX, pp. 250-255, 8 pages.
International Preliminary Report on Patentability issued in International PCT Application No. PCT/US2010/044873, dated Feb. 23, 2012, 16 pages.
International Search Report issued in International PCT Application PCT/US2004/012368, dated Aug. 24, 2004, 7 pages.
International Preliminary Report on Patentability dated Apr. 29, 2014, in International PCT Application No. PCT/US2012/062059, 13 pages.
International Search Report and Written Opinion dated Jun. 14, 2013, in International PCT Application No. PCT/US2012/062059, 21 pages.
International Search Report and Written Opinion issued in International PCT Application No. PCT/US2010/044873, dated May 10, 2011, 22 pages.
International Search Report and Written Opinion issued in International PCT Application No. PCT/US2013/043995, dated Oct. 24, 2013, 9 pages.

(56) References Cited

OTHER PUBLICATIONS

International Search Report and Written Opinion issued in International PCT Application No. PCT/US2014/018829, dated Jun. 2, 2014, 10 pages.
Material Safety Data Sheet, Blend of Di-potassium Phosphate, Nitrogen, and Ag-Phite (DKP xtra), Product No. 3-18-20, Plant Food Systems, Inc., Undated, 1 page.
Material Safety Data Sheet, DICAMBA 480 Manufacturing Concentrate, Reg. No. 24774, Syngenta Crop Protection Canada, Inc., MSDS Preparation Date Dec. 31, 2008, 6 pages.
McCormack, M.L., et al., "Glyphosate and Triclopyr Mixtures to Control Forest Brush," 1981, Proceedings Northeastern Weed Science Society, Philadelphia, PA, vol. 35, p. 218.
McCormack, M.L., et al., "Timing Triclopyr and Glyphosate Treatments on Forest Brush," 1982, Proceedings Northeastern Weed Science Society, New York, NY, vol. 36, pp. 209-214.
McDonald, P.M., et al., "Response of Young Ponderosa Pines, Shrubs, and Grasses to Two Release Treatments," 1996, USDA Forest Service Res. Note PSW-RN-419-Web, 8 pages.
Nalewaja, J.D., et al., "Salt Antagonism of Glyphosate," 1991, Weed Science, 39:622-628, 8 pages.
Nalewaja, J.D., et al., "2,4-D Amine Antagonism by Salts," 1991, Weed Technology, 5/4:873-880, 9 pages.
Notice of Pesticide Registration, Roundup Pro Concentrate, EPA Ref. No. 524-529, issued on Oct. 5, 2000, 34 pages.
Obenshain, K.R., et al., "Spatial Analysis of Herbicide Decay Rates in Louisiana," 1997, Environmental Monitoring and Assessment, 48:307-316.
Owen, M.D.K., et al., "Evaluation of Nicosulfuron, Rimsulfuron, and Pyridate Applied Postemergence for Weed Control in Corn," 1995, NCWSS Research Report-V.52, Ames, IA, 149-152.
Peniuk, M.G., et al., "Absorption, Translocation, and Metabolosm are not the Basis for Differential Selectivity of Wild Mustart (*Sinapis argensis* L.)," 1992, WSSA Abstracts, No. 165, 32:55.
Pernak, et al., "Ionic Liquids with Herbicidal Anions," 2011, Tetrahedron, 67:4838-4844, XP028227648.
Pernak, et al., "2,4-D Based Herbicidal Ionic Liquids," 2012, Tetrahedron, 68:4267-4273M XP028479458.
Petersen, P.J., et al., "Dicamba Absorption and Translocation as Influenced by Formulation and Surfactant," 1985, Weed Science, 33:717-720.
Poovaiah, B.W., et al., "Effects of Inorganic Salts on Tissue Permeability," 1976, Plant Physiol., 58:182-185.
Potts, K.T., Comprehensive Heterocyclic Chemistry, vol. 5, 1984, p. 284.
Prigot et al., "Derivatives of Piperazine. XXII. Piperazinium Salts for Utilization in Identification of Organic Acids," 1948, J Am Chem Sac, 70:2758-2759, XP055056011.
Product Guide Book 2000, Dow AgroSciences, 43 pages.
Product Label, Garton 4 Specialty Herbicide, DowElanco, (Sep. 8, 1995), 15 pages.
Product Label, Garton 3A, DowElanco, EPA Reg. No. 62719-37 (Amended Nov. 11, 1996), 15 pages.
Product Label, Invader 600 Herbicide, Nufarm, NRA Approval No. 49998/0900, (2000), 4 pages.
Product Labels, Roundup Max, Group M Herbicide, Monsanto, (Date Unknown), 18 pages.
Product Label, Lontrel Herbicide, DowAgroSciences, NRA Label No. 31635/1102, approved Nov. 14, 2002, 12 pages.
Product Label, Roundup CT Broadacre Herbicide, Monsanto, (Mar. 31, 2000), 7 pages.
Product Label, Roundup CT Herbicide, Monsanto, NRA Approval No. 31394/1102, (Jun. 2002) 15 pages.
Product Label, Roundup PowerMax Herbicide, Monsanto, NRA Approval No. 55687/1202, (Nov. 2002 and Jan. 2, 2003), 13 pages.
Product Label and Material Safety Data Sheet for Eclipse® Glyphosate Tolerant Canola Herbicide Tank-Mix, Registration No. 26633 Pest Control Products Act, Label Code CN-26633/26634-002-E, Dow AgroSciences, 2002 and 2003, 12 pages.
Purdue, Herbicide Formulations (http://web.archive.org/web/*/http://www.agriculture.purdue.edu/fnr/html/faculty/holt/NRCASupplement.pdf) from 2007, 19 pages.
Quimby, P.C., Jr., et al., "Selectivity of Dicamba in Wheat and Wild Buckwheat," 1971, Weed Science, 19/5:598-601.
Ramirez-Ortega, R., et al., "Enhancement Effect of N, P and K on Glyphosate for Broomrape (*Orobanche crenata* Forsk.) Control in Faba Bean (*Vicia faba* L.)," 1992, FABIS Newsletter 31, pp. 37-39.
"Registered Pesticides 1992-1994" prepared by Pesticides Board Malaysia, 3 pages.
"Roundup CT Broadacre Herbicide, Public Chemical Registration Information System,http://services.apvma.gov.au/Pubcris WebClientldetails.do?view/~summary&pcode-316, downloadedJun. 20, 2013, 6 pages."
Safety Data Sheet—Clarity (Version 3.0), BASF The Chemical Company, May 2, 2013, 9 pages.
Sargent, J.A., "Chapter 10 Relatiohnship of Selectivity to Uptake and Movement," 1976, Herbicides, 2nd Ed, vol. 2, 303-312, 12 pages.
Scott, P.C., "Separation of Effects of Auxin and Ethylene in Pea Roots," 1970, Nature, 226:1366-1367.
Seifert, J.R., et al., "Pre and Post Herbicide Applications on Hardwood Seedlings," 1992, Proceedings North Central Weed Science Society, Chicago, IL, 47:98.
Serafini, dicamba, diglycolamine salt (Clarity) Active Ingredient Registration 6/00, (http://pmep.cce.cornell.edu/profiles/herb-growthreg/dalapon-ethephon/diglycolamine/Diglycolamine_600.html), downloaded Apr. 6, 2014, 3 pages.
Site Management and Productivity in Tropical Plantation Forests: A Progress Report (bears the date of Dec. 1999), 14 pages.
Sparacino, A.C., et al., "Le Controle Des *Rubus* spp. Presentes Sur Les Rives Des Canaux D'Irrigation et Des Rizieres," 1993, Proceedings 45th International Symposium on Crop Protection, Part III, University of Gent, MFLRA3 58(a), p. 1018-1025.
Sprankle, P., et al., Rapid Inactivation of Glyphosate in the Soil, 1975, Weed Science, 23/3:224-228.
Supplemental Labeling regarding Roundup Pro Herbicide by Monsanto, EPA Reg. No. 524-475 (Nov. 1995), 10 pages.
Table 4-10, Chapter 4, "Triclopyr", Herbicide Risk Assessment, Marin Municipal Water District, 2010, http://www.marinwater.org/documentcenter/view/254, p. 4-39, downloaded Oct. 13, 2015, XP04760094, 1 page.
The Herbicide Glyphosate, 1985, Grossbard and Atkinson, Eds., Butterworth & Co. (Publishers) Ltd., p. 223.
Theilig, G., et al., "Imidazolsynthesen mit Formamid (Formamid-Reaktionen, L Mitteil.)," 1953, Chemische Berichte, 86:99-95, XP055056002.
Vermeulen, J.D., et al., A Guide to the Use of Herbicides, 1993, Dept of Agriculture, Republic of South Africa, 14th Ed., pp. 112-123.
Wagner, E., et al., "Coupling of adenovirus to transferrin-polylysine/DNA complexesgreatly enhances receptor-mediated gene delivery andexpression of transfected genes," 1992, PNAS, 89/13:6099-6103.
Wait, J.D., et al., "Weed Control in Glyphosate Resistant Corn," 2002, North Central Weed Science Society Research Report, 59:133-134.
Wan, Y., et al., "Generation of Large Numbers of Independently Transformed Fertile Barley Plants," 1994, Plant Physiology, 104:37-48.
Wauchope, R.D., et al, "The SCS/ARS/CES Pesticide Properties Database for Environmental Decision-Making," 1992, Rvws of Environ Contam and Toxic, 123:1-164.
Wright, G.M., et al., "Understory Vegetation Control to Establish Oak Regeneration," 1983, North Central Weed Control Conference Proceedings, Columbus, Ohio, 38:139, 3 pages.
Abdelghani, A.A., "Assessment of the Exposure of Workers Applying Herbicide Mixtures (2, 4-D+Roundup, Garlon-3A+Roundup), Toxicity and Fate of These Mixtures in the Environment," Summary Report, 1995, Conducted for Louisiana Department of Transportation and Development, Louisiana Transportation Research Center in Cooperation with U.S. Department of Transportation Federal Highway Administration, State Project #736-14/0067, No. 90-6ss, 70 pages.

(56) References Cited

OTHER PUBLICATIONS

Abdelghani, A.A., et al., "Toxicity Evaluation of Single and Chemical Mixtures of Roundup, Garlon-3A, 2,4-D, and Syndets Surfactant to Channel Catfish (*Ictalurus punctatus*), Bluegill Sunfish (*Lepomis microchirus*), and Crawfish (*Procambarus* spp.)," 1997, Evaluation of Single and Chemical Mixtures, J. Wiley & Sons, Inc., pp. 237-243.
Agrian, Buffer Protect, Westbridge Agricultural Products, http://www.agrian.com/labelcenter, downloaded Jan. 17, 2013, 2 pages.
Arif, A., et al., "Lalang Grass Control with Low Spray Volume of Glyphosate Herbicide," 1986, Symposium in Weed Science, Biotrop Special Publication No. 24, pp. 317-324.
Arsenovic, M., et al., "Weed Control on Railways in Yugoslavia," Brighton Crop Protection Conference—Weeds—1991, vol. 3, pp. 1159-1164.
Behrens, R., et al., "Dicamba Volatility," 1979, Weed Science, 27/5:486-493.
Bower, R., et al., "Transgenic Sugarcane Plants via Microprojectile Bombardment," 1992, The Plant Journal, 2/3:409-416.
Branham, B.E., et al., "Drift and Volatility of Broadleaf Herbicides," pp. 126-129.
Bytebier, B., et al., "T-DNA Organization in Tumor cultures and Transgenic Plants of the Monocotyledon Asparagus Officinalis," PNAS, USA, Genetics, 84:5345-5349.
Chambers, A., "Field Crop Herbicide Guide 1997-1998", Institute for Integrated Agricultural Development, RMB 1145, Rutherglen, 3685, Kondinin Group, Publisher, pp. 337-338.
Chee, Y.K., et al., "Sheep Grazing Reduces Chemical Weed Control in Rubber," 2002, Australian Centre for International Agriculture Research, Carberra, Australia, pp. 120-123.
Chorbadjian, R., et al., Interaction Between Glyphosate and Fluroxypyr Improve Mallow Control;2002, Crop Protection, 21:689-692.
Christou, P., "Stable Transformation of Soybean Callus by DNA-Coated Gold Particles," 1988, Plant Physiol, 87:671-674.
CLARITY®, Safety Data Sheet, BASF, Revised Aug. 14, 2006, 7 pages.
CLIMB® Alkalinity Agent, Wilbur-Ellis Company, CA Reg. No. 2935-50181, WA Reg. No. 2935-09001, F-091809-1, 2 pages.
COGNIS, "Functional Products Agnique PG 8107-G," Sep. 3, 2009, 2 pages.
Daggett, R.H., et al., "Long-Term Effects of Herbicide and Precommercial Thinning on Young Spruce-Fir Stands: The Austin Pond Study," Silviculture Research, Cooperative Forestry Research Unit Annual Report 2001-2002, University of Maine, pp. 29-31.
Dion, H.M., et al., "Competitive Sorption Between Glyphoste and Inorganic Phosphate on Clay Minerals and Low Organic Matter Soils," 2001, J Radioanaly and Nucl Chem, 249/2:385-390.
O'Sa, et al., "4,5-Dimethylimidazole: A Correction and Alternative Synthesis," 1991, J Heterocyclic Chem, 28, 1819-1920, XP055055998.
Duff, et al., "Identification of Carboxylic Acids: Use of N-Methylpiperazine and N-Phenylpiperazine," 1969, J Chem Ed, ACS, 46:388-390, XP009141119.
EPA Application for Pesticide, Accord Herbicide, ID No. 200405 (Sep. 1995), 32 pages.
Foy, C.L., et al., "Effect of Inhibitors and herbicides on Tricarboxylic Acid Cycle Substrate Oxidation by Isolated Cucumber Mitochondria," 1965, Weeds, 13/3:226-231.
Fraley, R.T., et al., "Expression of Bacterial Genes in Plant Cells," 1983, PNAS, 80:4803-4807.
Fromm, M.E, et al., "Expression of Genes Transferred into Monocot and Dicot Plant Cells by Electroporation," 1985, PNAS, 82/17:5824-5828.
Fynan, E.F., et al., DNA Vaccines: Protective Immunizations by Parenteral, Mucosal, and Gene-Gun Inoculations, 1993, PNAS, 90:11478-11482.
Giesemann, et al., "Untersuhungen über 1-Triphenylmethyl-imidazole, I," 1959, Chemische Berichte, 92:92-96, XP055056003.
Gilchrist, T.L. Heterocyclic Chemistry, Second Ed., 1992, Longman Group United Kingdom, pp. 283-293, 13 pages.
Gordon-Kamm, W.J., et al., "Transformation of Maize Cells and Regeneration of Fertile Transgenic Plants," 1990, The Plant Cell, 2:603-618.
Hall, J.K., et al., "Dicamba Mobility in Conventionally Tilled and Non-Tilled Soils," 1994, Soil & Tillage Res, 30:3-17.
Hartzler, B., "Dicamba Volatility," 2001, Weed Science Online, Iowa State University, Downloaded Mar. 27, 2014, 4 pages.
Harahap, W., "The Study of Glyphosate and its Mixture in Controlling General Weeds in Rubber Planting Strips," Symposium in Weed Science, BIOTROP Spec. Publ. No. 24, 1986, pp. 349-357.
Hatzios, et al., "Pelargonic Acid," 1998, WAASA Herbicide handbook, pp. 55-57, 3 pages, XP002953604.
Hoefer, R.H., et al., "Absorption of Dicamba in Soybeans as Effected by Formulation and Suractants," 1979, North Central Weed Control Conference, Abstract, pp. 4-5.
Holt, H.A., et al., "Controlling Woody Plants with Wiping Application," 1986, Proceedings Southern Weed Science Society, Weed Science and Risk Assessment, 39th Annual Meeting, Nashville, TN, p. 364.
Howell, R.K., et al., "Low Volume Foliar Applications of Triclopyr, Picloram, Imazapyr and Glyphosate Mixtures for Rights-of-Way Cleanup," 1998, Proceedings Southern Weed Science Society, Preparing for the New Millennium, 51st Annual Meeting, Birmingham, Alabama, pp. 195-197.
Jackson, N.E., "Control of Brush and Chaparral Species with Glyphosate," 1986, Proceedings 38th Annual California Need Conference, Fresno, California, pp. 221-223.
Kay, S.H., et al., "Effects of Tank Mixing Triclopyr Amine and Glyphosate on Control of Alligatorweed," 1992, Proceedings Southern Weed Science Society, 45th Annual Meeting, Little Rock, Arkansas, p. 291.
Lawlor, F.M., et al., Response of swallow-wort to herbicides (2001), Weed Science, vol. 50, No. 2, Abstract only, 1 page.
Lawrie, J., et al., Effects of herbicide mixtures and additives on Rhododendron ponticum, Weed Research, vol. 33, pp. 25-34 (1993).
Little, K., et al., "Control of Eucalyptus grandis Cut Stumps," 1998, ICFR Bulletin Series, No. 02/98, 16 pages.
Little, K., et al., First Rotation Eucalyptus macarthurii Cut Stump Control in KwaZulu-Natal, South Africa, South African Forestry Journal No. 207, pp. 15-20, Jul. 2006.
Little, K., et al., "The Killing of Eucalyptus grandis Multiple-Stem Cut-Stumps in the Karkloof Project," ICFR Bulletin Series, No. 03/00, 6 pages.
Lu, L., et al., "High Efficiency Retroviral Mediated Gene Transduction into Single Isolated Immature andReplatable CD343 + Hematopoietic Stem/ProgenitorCells from Human Umbilical Cord Blood," 1993, J Exp Med, 178/6:2089-2096.
LUPASOL® Products, Technical Information, Feb. 2008, BASF, 12 pages.
LUPASOL®, Polyethylenimines for Creative Connections, BASF, EVD 0116e 11.2005, pp. 6.
Material Safety Data Sheet regarding Amine 4 2,4-D Weed Killer prepared by Registrations and Regulatory Affairs, Date of Issue Dec. 14, 2012, 3 pages.
Material Safety Data Sheet, Concentrate Roundup PowerMAX Weedkiller, Scotts, (Apr. 15, 2004), 4 pages.
Material Safety Data Sheet, BANVEL II®, BASF, Revised Nov. 30, 2006, 5 pages.
Material Safety Data Sheet, BANVEL®, EPA Reg. No. 51036-289, BASF, Prepared Jul. 14, 1999, 3 pages.

\* cited by examiner

HERBICIDAL COMPOSITIONS CONTAINING N-PHOSPHONOMETHYL GLYCINE AND AN AUXIN HERBICIDE

REFERENCE TO RELATED APPLICATIONS

This application is a continuation of U.S. patent application Ser. No. 12/802,395, filed Jun. 4, 2010, which is a continuation of U.S. patent application Ser. No. 11/077,279, filed Mar. 10, 2005, which claims the benefit of U.S. Provisional Application Ser. No. 60/552,065, filed Mar. 10, 2004, the entire contents of each of which are incorporated herein by reference.

BACKGROUND

The present invention relates generally to herbicidal compositions or formulations, and to methods of using such compositions to kill or control the growth and proliferation of unwanted plants. In particular, the present invention relates to herbicidal compositions, as well as their methods of use, which comprise N-phosphonomethylglycine (glyphosate), or a herbicidal derivative thereof, and an auxin herbicide, or a herbicidal derivative thereof, optionally with one or more suitable surfactants. Such compositions cause early visual symptoms of treatment and/or enhanced effectiveness or control when applied to the foliage of plants.

Glyphosate is well known in the art as an effective post-emergent foliar-applied herbicide. In its acid form, glyphosate has a structure represented by the formula:

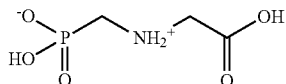

and is relatively insoluble in water (1.16% by weight at 25° C.). For this reason it is typically formulated as a water-soluble salt.

Among the water soluble salts of glyphosate is the potassium salt, having a structure represented by the formula:

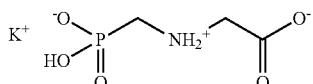

in the ionic form predominantly present in aqueous solution at a pH of about 4. Glyphosate potassium salt has a molecular weight of 207. This salt is disclosed, for example, by Franz in U.S. Pat. No. 4,405,531, as one of the "alkali metal" salts of glyphosate useful as herbicides, with potassium being specifically disclosed as one of the alkali metals, along with lithium, sodium, cesium and rubidium. Example C discloses the preparation of the monopotassium salt by reacting the specified amounts of glyphosate acid and potassium carbonate in an aqueous medium.

Herbicidal compositions comprising the herbicide N-phosphonomethyl-glycine or derivatives thereof ("glyphosate"), are useful for suppressing the growth of, or killing, unwanted plants such as grasses, weeds and the like. Glyphosate typically is applied to the foliage of the target plant. After application the glyphosate is absorbed by the foliar tissue of the plant and translocated throughout the plant. Glyphosate noncompetitively blocks an important biochemical pathway which is common to virtually all plants, but which is absent in animals. Although glyphosate is very effective in killing or controlling the growth of unwanted plants, the uptake (i.e., absorption) of glyphosate by the plant foliar tissue and translocation of glyphosate throughout the plant is relatively slow. Visual symptoms that a plant has been treated with glyphosate may not appear until one week or more after treatment.

There is a continuing need for herbicidal compositions which exhibit long-term control of unwanted plants and exhibit early visual symptoms of treatment. These compositions would be well suited to applications in cooler temperatures wherein the early visual symptoms may be readily seen while the long-term control would improve as temperatures increase.

As will be clear from the disclosure that follows, these and other benefits are provided by the present invention.

SUMMARY OF THE INVENTION

The present invention provides herbicidal compositions comprising glyphosate or a herbicidal derivative thereof, an auxin herbicide or a herbicidal derivative thereof, and at least one surfactant. The present invention also provides methods for killing or controlling the growth of plants by contacting the foliage of the plants with the diluted concentrate composition.

One embodiment of the present invention is directed to an aqueous herbicidal concentrate composition comprising glyphosate or a herbicidal derivative thereof, an auxin comprising one or more auxin herbicides selected from the group consisting of 2,4-D, 2,4-DB, dichlorprop, MCPA, MCPB, mecoprop, dicamba, picloram, quniclorac and agriculturally acceptable salts or esters thereof and a surfactant component in solution or stable suspension, emulsion or dispersion, comprising one or more surfactants. The glyphosate (acid equivalent basis) and the auxin herbicide (acid equivalent basis) are present in a weight ratio of at least 32:1 and the composition has a cloud point of at least about 50 C and a crystallization point not higher than about 0 C.

Another embodiment of the present invention is directed to an aqueous herbicidal concentrate composition comprising glyphosate, predominantly in the form of the potassium salt thereof in a concentration of at least 65 grams acid equivalent per liter, and an auxin herbicide comprising one or more auxin herbicides selected from the group consisting of 2,4-D, 2,4-DB, dichlorprop, MCPA, MCPB, mecoprop, dicamba, picloram, quniclorac and agriculturally acceptable salts or esters thereof. The herbicidal concentrate composition further comprises a first surfactant component in solution or stable suspension, emulsion or dispersion comprising one or more surfactants selected from the group consisting of secondary or tertiary amines, dialkoxylated quaternary ammonium salts, monoalkoxylated quaternary ammonium salts, quaternary ammonium salts, ether amines, amine oxides, dialkoxylated amines, aminated alkoxylated alcohols, alkyl alkoxylated phosphates and alkylpolyglycosides.

Yet another embodiment of the present invention is directed to an aqueous herbicidal concentrate composition comprising glyphosate, predominantly in the form of the isopropylammonium salt thereof in a concentration of greater than 360 grams acid equivalent per liter, an auxin herbicide component comprising one or more auxin herbicides selected from the group consisting of 2,4-D, 2,4-DB, dichlorprop, MCPA, MCPB, mecoprop, dicamba, picloram, quniclorac and agriculturally acceptable salts or esters thereof, and a surfactant component in solution or stable suspension, emulsion or dispersion, comprising one or more surfactants. The glyphosate (acid equivalent basis) and the auxin herbicide component (acid equivalent basis) are present in a weight ratio of at least 9.5:1 and the composition has a cloud point of at least about 50 C and a crystallization point not higher than about 0° C.

Another embodiment of the present invention is directed to a method of killing or controlling weeds or unwanted plants comprising diluting an aqueous herbicidal concentrate composition in an amount of water to form an application mixture and applying a herbicidally effective amount of the application mixture to foliage of the weeds or unwanted plants, wherein the weeds or unwanted plants comprise *Commelina* and the aqueous herbicidal concentrate composition comprises glyphosate or a herbicidal derivative thereof, an auxin herbicide component comprising one or more auxin herbicides selected from the group consisting of 2,4-D, 2,4-DB, dichlorprop, MCPA, MCPB, mecoprop, dicamba, picloram, quniclorac and agriculturally acceptable salts or esters thereof, and a surfactant component in solution or stable suspension, emulsion or dispersion, comprising one or more surfactants.

Other objects and features of the present invention will be in part apparent and in part pointed out hereinafter.

DETAILED DESCRIPTION

According to the present invention, herbicidal compositions containing glyphosate or a derivative thereof, an auxin herbicide or a derivative thereof, and a suitable surfactant, are provided that are advantageous for a number of reasons, including early visual symptoms of plant treatment, rapid uptake by the target plant, and control of a broad spectrum of plant species, as well as enhanced, more consistent control of unwanted plants. Although use of reduced application rates is not preferred, in at least some embodiments, lower application rates may be used without a significant loss of effectiveness of plant control.

Among the various aspects of the present invention is an aqueous herbicidal composition of N-phosphonomethyl glycine (glyphosate), predominantly in the form of the potassium salt thereof, and an auxin herbicide. The word "predominantly" in the above context means that at least about 50%, preferably at least about 55, 60, 65, 70, 75, 80, 85, 90 or about 95%, by weight of the glyphosate, expressed as a.e., is present as the potassium salt. Other salts of glyphosate which can make up the balance of the glyphosate component are agriculturally acceptable salts including the isopropylamine, di-ammonium, ammonium, sodium, monoethanolamine, n-propylamine, methylamine, ethylamine, hexamethylenediamine, dimethylamine or trimethylsulfonium salts. The second salt ion should be chosen so as not to adversely affect the viscosity, cloud point, non-crystallization and other stability properties of the composition.

Another aspect of the present invention is an aqueous herbicidal composition of N-phosphonomethyl glycine (glyphosate), predominantly in the form of the isopropylamine salt thereof, and an auxin herbicide. Other salts of glyphosate which can make up the balance of the glyphosate component are agriculturally acceptable salts including the di-ammonium, ammonium, sodium, potassium, monoethanolamine, n-propylamine, methylamine, ethylamine, hexamethylenediamine, dimethylamine or trimethylsulfonium salts.

The auxin herbicide is selected from the group consisting of 2,4-dichlorophenoxyacetic acid (2,4-D), 4-(2,4-dichlorophenoxy)butanoic acid (2,4-DB), dichloroprop, (4-chloro-2-methylphenoxy)acetic acid (MCPA), 4-(4-chloro-2-methylphenoxy)butanoic acid (MCPB), mecoprop, dicamba, picloram, quinclorac, agriculturally acceptable salts or esters of any of these herbicides, and mixtures thereof. In one embodiment, preferably, the auxin herbicide is selected from the group consisting of 2,4-dichlorophenoxyacetic acid (2,4-D), dicamba, salts or esters thereof, and mixtures thereof. Generally, the primary action of auxin herbicides appears to involve cell wall plasticity and nucleic acid metabolism. 2,4-D is thought to acidify the cell wall by stimulating the activity of a membrane-bound ATPase-driven proton pump. The reduction in apoplasmic pH induces cell elongation by increasing the activity of certain enzymes responsible for cell wall loosening. Low concentrations of 2,4-D are reported to stimulate RNA polymerase, resulting in subsequent increases in RNA, DNA, and protein biosynthesis. Abnormal increases in these processes presumably lead to uncontrolled cell division and growth, which results in vascular tissue destruction. In contrast, high concentrations of 2,4-D and other auxin-type herbicides inhibit cell division and growth, usually in meristematic regions that accumulate photosynthate assimilates and herbicide from the phloem.

In another embodiment, preferably, the auxin herbicide is at least 1% soluble by weight in water at pH 6. The auxin herbicide can be present in the composition in the form of its acid, an agriculturally acceptable salt (e.g., isopropylamine, di-ammonium, ammonium, sodium, monoethanolamine, n-propylamine, methylamine, ethylamine, hexamethylenediamine, dimethylamine or trimethylsulfonium), or an agriculturally acceptable ester (e.g., methyl, ethyl, propyl, butyl, octyl, ethoxyethyl, butoxyethyl or methoxypropyl). The salt or ester ion of the auxin herbicide should be chosen to not affect the viscosity, cloud point, non-crystallization and other stability properties of the composition.

In another aspect of the present invention, the glyphosate and auxin herbicide compositions may contain 5 g a.e./L (grams acid equivalent per liter) to 600 g glyphosate a.e./L, preferably from 65 to about 600, from about 75 to about 600, from about 100 to about 600, from about 150 to about 600, from about 200 to about 600, from about 250 to about 600, from about 300 to about 600, from about 350 to about 600, from about 400 to about 600, from about 450 to about 600, or from about 480 to about 600 g glyphosate a.e./L. In this context, generally, the weight ratio of the glyphosate (acid equivalent basis) to the auxin herbicide (acid equivalent basis) varies depending on the activity of the auxin herbicide which is generally determined using the standard use rates. A person skilled in the art would know that a higher standard use rate indicates a lower activity and thus more of the auxin herbicide should be used to achieve acceptable results. With this relationship in mind, in one embodiment, typically, the weight ratio of glyphosate to 2,4-D, 2,4-DB, MCPA, or MCPB is about 10:1 to about 100:1. In another embodiment, typically, the weight ratio of glyphosate to mecoprop is about 10:1 to about 50:1. In yet another embodiment, typically, the weight ratio of glyphosate to dicamba, or picloram is about 20:1 to about 200:1. In a further embodiment, preferably, the weight ratio of glyphosate to 2,4-D is about 20:1 to about 100:1; more preferably, about 20:1 to about 50:1; particularly, about 25:1 to about 50:1. In yet a further embodiment, preferably, the weight ratio of glyphosate to dicamba is about 40:1 to about 200:1; more preferably, about 40:1 to about 100:1; particularly, about 50:1 to about 100:1.

In another embodiment of the invention, the glyphosate in the glyphosate and auxin herbicide compositions is present in an amount of at least about 75, 100, 125, 150, 175, 200, 225, 250, 275, 300, 325, 350, 375, 400, 425, 450, 475, 480, 500, 525, 550, 575, 580 or 600 g a.e./L.

In another embodiment, the glyphosate (a.e. basis) and auxin herbicide component (a.e. basis) are present in compositions of the invention in a weight ratio of at least 33:1, 34:1, 35:1, 36:1, 37:1, 38:1, 39:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1 or 200:1. In another embodiment, the glyphosate (a.e. basis) and auxin herbicide component (a.e. basis) are present in a weight ratio of from about 40:1 to about 200:1, from about 50:1 to about 200:1, from about 60:1 to about 200:1, from about 50:1 to about 150:1, from about 50:1 to about 100:1 or from 32:1 to about 50:1.

In another embodiment, the glyphosate (a.e. basis) and auxin herbicide component (a.e. basis) are present in compositions of the invention in a weight ratio of at least about 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1 or 200:1. Preferably, the glyphosate is present in an amount of at least 65 g a.e./L. In one embodiment, the glyphosate concentration is between 360 and 445 g a.e./L, and the glyphosate (a.e. basis) and auxin herbicide component (a.e. basis) are present in a weight ratio of about 5:1 to about 50:1, about 5:1 to about 40:1, or about 8:1 to about 36:1. In a second embodiment, the glyphosate concentration is between 445 and 480 g a.e./L, and the glyphosate (a.e. basis) and auxin herbicide component (a.e. basis) are present in a weight ratio of about 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, or 65:1. In a third embodiment, the glyphosate concentration is between 360 and 525 g a.e./L, and the glyphosate (a.e. basis) and auxin herbicide component (a.e. basis) are present in a weight ratio of about 8:1 to about 80:1 or about 25:1 to about 56:1. In a fourth embodiment, the glyphosate concentration is at least 480 g a.e./L, and the glyphosate (a.e. basis) and auxin herbicide component (a.e. basis) are present in a weight ratio of about 25:1 to about 80:1, about 50:1 to about 80:1, about 63:1 to about 80:1, or about 25:1 to about 52:1.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. Typical application rates of the glyphosate and auxin herbicide compositions of the present invention can be determined from the label of each commercially available herbicide for a particular weed species. In general, the application rate of glyphosate is about 340 grams per acre. A person skilled in the art would understand that when the weed growth is heavy or dense or where weeds are growing in an undisturbed area, a higher application rate may be necessary to achieve acceptable weed control. In addition, for difficult-to-control weeds, a higher application rate may be necessary for adequate weed control.

The potassium glyphosate and auxin herbicide composition of the present invention is useful in controlling a variety of broadleaf weeds. These weeds include Velvetleaf, Redroot Pigweed, Pigweed Species, Tall Waterhemp, Giant Ragweed, Indian Mustard, Sicklepod, Lambsquarters, Wild Poinsettia, Common Mallow, Hemp Sesbania, Prickly Sida, Wild Mustard, Morningglory (Brazil), Morningglory, Ivyleaf Morningglory, Pitted Morningglory, Buckwheat, Cutleaf Evening Primrose, Curly Dock, Common Chickweed, Common Dayflower and Tropical Spiderwort.

Also provided by the present invention is a method of killing or controlling weeds or unwanted vegetation comprising diluting with a suitable volume of water a herbicidally effective amount of a composition as provided herein to form an application mixture, and applying the application mixture to foliage of the weeds or unwanted vegetation. If desired, the user can mix one or more adjuvants with a composition of the invention and the water of dilution when preparing the application composition. Such adjuvants can include additional surfactant and/or an inorganic salt such as ammonium sulfate with the aim of further enhancing herbicidal efficacy. However, under most conditions a herbicidal method of use of the present invention gives acceptable efficacy in the absence of such adjuvants.

In a particular contemplated method of use of a composition of the invention, the composition, following dilution in water, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include varieties of wheat, turfgrass, and corn.

Plant treatment compositions can be prepared simply by diluting a concentrate composition of the invention in water. Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Useful spray volumes for the present invention can range from about 10 to about 1000 liters per hectare (l/ha) or higher, by spray application.

High Load

In a further embodiment, the glyphosate and auxin herbicide compositions may contain about 300 to about 600 g a.e./L of glyphosate, predominantly in the form of the potassium salt thereof. For these compositions, the balance of the glyphosate component is made up of agriculturally acceptable salts including the isopropylamine, monoethanolamine, n-propylamine, methylamine, ethylamine, ammonium, diammonium, hexamethylenediamine, dimethylamine or trimethylsulfonium salts. In another embodiment, preferably, the glyphosate and auxin herbicide compositions may contain about 450 to about 600 g a.e./L of glyphosate, predominantly in the form of the potassium salt thereof. In general, as the concentration of glyphosate is increased in the composition, the concentration of the auxin herbicide may be decreased to achieve acceptable weed control. Typically, for potassium glyphosate and auxin herbicide compositions containing about 450 to about 600 g a.e./L of glyphosate, the weight ratio of the glyphosate to the auxin herbicide is about 25:1 to about 100:1. In particular, for potassium glyphosate and 2,4-D compositions containing about 540 to about 600 g a.e./L of glyphosate, the weight ratio of the glyphosate to 2,4-D is about 25:1 to about 50:1.

In another embodiment, the glyphosate and auxin herbicide compositions may contain about 360 to about 600 g a.e./L of glyphosate, predominantly in the form of the isopropylamine salt thereof. For these compositions, the balance of the glyphosate component is made up of agriculturally acceptable salts including the monoethanolamine, n-propylamine, methylamine, ethylamine, ammonium, diammonium, potassium, hexamethylenediamine, dimethylamine or trimethylsulfonium salts. In another embodiment, preferably, the glyphosate and auxin herbicide compositions may contain about 360 to about 450 g a.e./L of glyphosate, predominantly in the form of the isopropylamine salt thereof. In general, as the concentration of glyphosate is increased in the composition, the concentration of the auxin herbicide may be decreased to achieve acceptable weed control. Typically, for isopropylamine glyphosate and auxin herbicide compositions containing about 360 to about 450 g a.e./L of glyphosate, the weight ratio of the glyphosate to the auxin herbicide is about 10:1 to about 20:1. In one embodiment, the glyphosate is present in an amount of at least about 370, 380, 390, 400, 410, 420, 430, 440, 450, 475, 480, 500, 525, 550, 575, 580 or 600 g a.e./L, and the glyphosate (a.e. basis) and auxin herbicide component (a.e. basis) are present in a weight ratio of at least 9.5:1, 9.6:1, 9.7:1, 9.8:1, 9.9:1, 10:1, 11:1, 12:1, 13:1, 14:1, 15:1, 16:1, 17:1, 18:1, 19:1, or 20:1. In a second embodiment, the glyphosate is present in an amount of from about 400 to about 600, from about 420 to about 600, from about 430 to about 600, from about 440 to about 600, from about 450 to about 600, or from about 480 to about 600 g a.e./L, and the glyphosate (a.e. basis) and auxin herbicide component (a.e. basis) are present in a weight ratio of at least 9.5:1, 9.6:1, 9.7:1, 9.8:1, 9.9:1, 10:1, 11:1, 12:1, 13:1, 14:1, 15:1, 16:1, 17:1, 18:1, 19:1, or 20:1.

Surfactants

Surfactants and cosurfactants effective in formulating glyphosate, such as potassium or isopropylamine glyphosate, with auxin herbicides include cationic, nonionic, anionic, and amphoteric surfactants and cosurfactants as described below and mixtures thereof, wherein the surfactant component is present in an amount of at least about 5 wt. % based on the total weight of the composition.

Cationic surfactants and cosurfactants effective in such glyphosate formulations include:

(a) a secondary or tertiary amine having the formula:

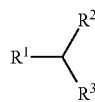

(1)

wherein $R^1$ is hydrocarbyl having from 1 to about 30 carbon atoms, and $R^2$ and $R^3$ are hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl or alkenyl group having from about 12 to about 22 carbon atoms, and $R^2$ and $R^3$ are independently hydrogen, methyl or ethyl. In one embodiment of the amine of formula (1), $R^1$ is a linear or branched alkyl group having from about 12 to about 22 carbon atoms, and $R^2$ and $R^3$ are independently linear or branched hydroxyalkyl groups having from 1 to about 6 carbon atoms.

(b) dialkoxylated quaternary ammonium salt having the formula:

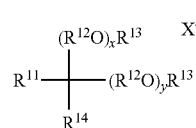

(2)

wherein $R^{11}$ is hydrocarbyl or substituted hydrocarbyl having from 1 to about 30 carbon atoms, $R^{12}$ in each of the $(R^{12}O)_x$ and $(R^{12}O)_y$ groups is independently $C_2$-$C_4$ alkylene, $R^{13}$ is hydrogen, or a linear or branched alkyl group having from 1 to about 4 carbon atoms, $R^{14}$ hydrocarbyl or substituted hydrocarbyl having from 1 to about 30 carbon atoms, x and y are independently an average number from 1 to about 40, and $X^-$ is an agriculturally acceptable anion. In this context, preferred $R^{11}$ and $R^{14}$ hydrocarbyl groups are linear or branched alkyl, linear or branched alkenyl, linear or branched alkynyl, aryl, or aralkyl groups. Preferably, $R^{11}$ and $R^{14}$ are independently a linear or branched alkyl or linear or branched alkenyl group having from 1 to about 25 carbon atoms, $R^{12}$ in each of the $(R^{12}O)_x$ and $(R^{12}O)_y$ groups is independently $C_2$-$C_4$ alkylene, $R^{13}$ is hydrogen, methyl or ethyl, and the sum of x and y is an average number from about 2 to about 30. More preferably, $R^{11}$ and $R^{14}$ are independently a linear or branched alkyl group having from 1 to about 22 carbon atoms, $R^{12}$ in each of the $(R^{12}O)_x$ and $(R^{12}O)_y$ groups is independently ethylene or propylene, $R^{13}$ is hydrogen or methyl, and the sum of x and y is an average number from about 2 to about 20. Even more preferably, $R^{11}$ is a linear or branched alkyl group having from about 8 to about 22 carbon atoms and $R^{14}$ is a linear or branched alkyl group having from 1 to about 22 carbon atoms, $R^{12}$ in each of the $(R^{12}O)_x$ and $(R^{12}O)_y$ groups is independently ethylene or propylene, $R^{13}$ is hydrogen or methyl, and x is an average number from about 2 to about 20. Most preferably, $R^{11}$ is a linear or branched alkyl group having from about 8 to about 22 carbon atoms and $R^{14}$ is a linear or branched alkyl group having from 1 to about 6 carbon atoms, $R^{12}$ in each of the $(R^{12}O)_x$ and $(R^{12}O)_y$ groups is independently ethylene or propylene, $R^{13}$ is hydrogen or methyl, and x is an average number from about 2 to about 15, or $R^{11}$ and $R^{14}$ are independently a linear or branched alkyl group having from about 8 to about 22 carbon atoms, $R^{12}$ in each of the $(R^{12}O)_x$ and $(R^{12}O)_y$ groups is independently ethylene or propylene, $R^{13}$ is hydrogen or methyl, and x is an average number from about 5 to about 15. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

(c) monoalkoxylated quaternary ammonium salts having the formula:

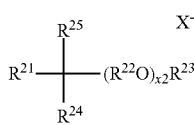

(3)

wherein $R^{21}$ and $R^{25}$ are independently hydrogen or hydrocarbyl or substituted hydrocarbyl having from 1 to about 30 carbon atoms, $R^{24}$ is hydrocarbyl or substituted hydrocarbyl having from 1 to about 30 carbon atoms, $R^{22}$ in each of the $(R^{22})_{x2}$ groups is independently $C_2$-$C_4$ alkylene, $R^{23}$ is hydrogen, or a linear or branched alkyl group having from 1 to about 30 carbon atoms, $x^2$ is an average number from 1 to about 60, and $X^-$ is an agriculturally acceptable anion. In this context, preferred $R^{21}$, $R^{24}$, and $R^{25}$ hydrocarbyl groups are linear or branched alkyl, linear or branched alkenyl, linear or branched alkynyl, aryl, or aralkyl groups. Preferably, $R^{21}$, $R^{24}$ and $R^{25}$ are independently a linear or branched alkyl or linear or branched alkenyl group having from 1 to about 25 carbon atoms, $R^{22}$ in each of the $(R^{22}O)_{x2}$ groups is independently $C_2$-$C_4$ alkylene, $R^{23}$ is hydrogen, methyl or ethyl, and $x^2$ is an average number from 1 to about 40. More preferably, $R^{21}$, $R^{24}$ and $R^{25}$ are independently a linear or branched alkyl group having from 1 to about 22 carbon atoms, $R^{22}$ in each of the $(R^{22}O)_{x2}$ groups is independently ethylene or propylene, $R^{23}$ is hydrogen or methyl, and $x^2$ is an average number from 1 to about 30. Even more preferably, $R^{21}$ is a linear or branched alkyl group having from about 8 to about 22 carbon atoms, $R^{22}$ in each of the $(R^{22}O)_{x2}$ groups is independently ethylene or propylene, $R^{23}$ is hydrogen or methyl, $R^{24}$ and $R^{25}$ are independently a linear or branched alkyl group having from 1 to about 22 carbon atoms, and $x^2$ is an average number from 1 to about 30. Even more preferably, $R^{21}$ is a linear or branched alkyl group having from about 8 to about 22 carbon atoms, $R^{22}$ in each of the $(R^{22}O)_{x2}$ groups is independently ethylene or propylene, $R^{23}$ is hydrogen or methyl, $R^{24}$ and $R^{25}$ are independently a linear or branched alkyl group having from 1 to about 6 carbon atoms, and $x^2$ is an average number from about 5 to about 25. Most preferably, $R^{21}$ is a linear or branched alkyl group having from about 16 to about 22 carbon atoms, $R^{22}$ in each of the $(R^{22}O)_{x2}$ groups is independently ethylene or propylene, $R^{23}$ is hydrogen or methyl, $R^{24}$ and $R^{25}$ are independently a linear or branched alkyl group having from 1 to about 3 carbon atoms, and $x^2$ is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(d) quaternary ammonium salts having the formula:

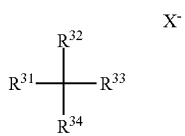

(4)

wherein $R^{31}$, $R^{33}$ and $R^{34}$ are independently hydrogen or hydrocarbyl or substituted hydrocarbyl having from 1 to about 30 carbon atoms, $R^{32}$ is hydrocarbyl or substituted hydrocarbyl having from 1 to about 30 carbon atoms, and $X^-$ is an agriculturally acceptable anion. In this context, preferred $R^{31}$, $R^{32}$, $R^{33}$, and $R^{34}$ hydrocarbyl groups are linear or branched alkyl, linear or branched alkenyl, linear or branched alkynyl, aryl, or aralkyl groups. Preferably, $R^{31}$ is a linear or branched alkyl or linear or branched alkenyl group having from about 8 to about 30 carbon atoms, and $R^{32'}$, $R^{33}$ and $R^{34}$ are independently a linear or branched alkyl or linear or branched alkenyl group having from 1 to about 30 carbon atoms. More preferably, $R^{31}$ is a linear or branched alkyl or linear or branched alkenyl group having from about 8 to about 22 carbon atoms, and $R^{32'}$, $R^{33}$ and $R^{34}$ are independently a linear or branched alkyl or linear or branched alkenyl group having from 1 to about 6 carbon atoms. Even more preferably, $R^{31}$ is a linear or branched alkyl group having from about 8 to about 16 carbon atoms, and $R^{32}$, $R^{33}$ and $R^{34}$ are independently a linear or branched alkyl group having from 1 to about 6 carbon atoms. Most preferably, $R^{31}$ is a linear or branched alkyl group having from about 8 to about 14 carbon atoms, and $R^{32}$, $R^{33}$ and $R^{34}$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(e) ether amines having the formula:

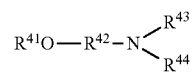

(5)

wherein $R^{41}$ is hydrocarbyl or substituted hydrocarbyl having from 1 to about 30 carbon atoms; $R^{42}$ is hydrocarbylene or substituted hydrocarbylene having from 2 to about 30 carbon atoms; $R^{43}$ and $R^{44}$ are independently hydrogen, hydrocarbyl or substituted hydrocarbyl having from 1 to about 30 carbon atoms, or $-(R^{45}O)_x{}^4R^{46}$, $R^{45}$ in each of the $(R^{45}O)_x{}^4$ groups is independently $C_2$-$C_4$ alkylene, $R^{46}$ is hydrogen, or a linear or branched alkyl group having from 1 to about 4 carbon atoms, and $x^4$ is an average number from 1 to about 50. In this context, preferred $R^{41}$, $R^{42}$, $R^{43}$, and $R^{44}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^{41}$ is a linear or branched alkyl, linear or branched alkenyl, linear or branched alkynyl, aryl, or aralkyl group having from 8 to about 25 carbon atoms, $R^{42}$ is a linear or branched alkylene or alkenylene group having from 2 to about 30 carbon atoms, $R^{43}$ and $R^{44}$ are independently hydrogen, a linear or branched alkyl, linear or branched alkenyl, linear or branched alkynyl, aryl, or aralkyl group having from 1 to about 30 carbon atoms, or $-(R^{45}O)_x{}^4R^{46}$, $R^{45}$ in each of the $(R^{45}O)_x{}^4$ groups is independently $C_2$-$C_4$ alkylene, $R^{46}$ is hydrogen, methyl or ethyl, and $x^4$ is an average number from 1 to about 30. More preferably, $R^{41}$ is a linear or branched alkyl or alkenyl group having from 8 to about 22 carbon atoms, $R^{42}$ is a linear or branched alkylene or alkenylene group having from 2 to about 6 carbon atoms, $R^{43}$ and $R^{44}$ are independently hydrogen, a linear or branched alkyl or alkenyl group having from 1 to about 6 carbon atoms, or $-(R^{45}O)_x{}^4R^{46}$, $R^{45}$ in each of the $(R^{45}O)_x{}^4$ groups is independently ethylene or propylene, $R^{46}$ is hydrogen or methyl, and $x^4$ is an average number from 1 to about 15. Most preferably, $R^{41}$ is a linear or branched alkyl or alkenyl group having from 8 to about 18 carbon atoms, $R^{42}$ is ethylene or propylene, $R^3$ and $R^4$ are independently hydrogen, methyl, or —$(R^{45}O)_x{}^4R^{46}$, $R^{45}$ in each of the $(R^{45}O)_x{}^4$ groups is independently ethylene or propylene, $R^{46}$ is hydrogen, and $x^4$ is an average number from 1 to about 5.

(f) amine oxides having the formula:

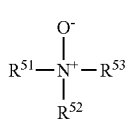

(6)

wherein $R^{51}$, $R^{52}$ and $R^{53}$ are independently hydrogen, hydrocarbyl or substituted hydrocarbyl, —$(R^{54}O)_x{}^5R^{55}$, or —$R^{56}(OR^{54})_x{}^5OR^{55}$, $R^{54}$ in each of the $x^5$ $(R^{54}O)$ groups is independently $C_2$-$C_4$ alkylene, $R^{55}$ is hydrogen, or a linear or branched alkyl group having from 1 to about 30 carbon atoms, $R^{56}$ is hydrocarbylene or substituted hydrocarbylene having from 2 to about 6 carbon atoms, $x^5$ is an average number from 1 to about 50, and the total number of carbon atoms in $R^{51}$, $R^{52}$ and $R^{53}$ is at least 8. In this context, preferred $R^{51}$, $R^{52}$, $R^{53}$, and $R^{56}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^{51}$ and $R^{52}$ are independently hydrogen, a linear or branched alkyl or linear or branched alkenyl group having from 1 to about 30 carbon atoms, or —$(R^{54}O)_x{}^5R^{55}$, $R^{53}$ is a linear or branched alkyl or linear or branched alkenyl group having from about 8 to about 30 carbon atoms, $R^{54}$ in each of the $(R^{54}O)_x{}^5$ groups is independently $C_2$-$C_4$ alkylene; $R^{55}$ is hydrogen, methyl or ethyl, and $x^5$ is an average number from 1 to about 30. More preferably, $R^{51}$ and $R^{52}$ are independently hydrogen, or a linear or branched alkyl group having from 1 to about 6 carbon atoms, and $R^{53}$ is a linear or branched alkyl group having from about 8 to about 22 carbon atoms; or $R^{51}$ and $R^{52}$ are independently —$(R^{54}O)_x{}^5R^{55}$, $R^{53}$ is a linear or branched alkyl group having from about 8 to about 22 carbon atoms, $R^{54}$ in each of the $(R^{54}O)_x{}^5$ groups is ethylene or propylene, $R^{55}$ is hydrogen or methyl, and $x^5$ is an average number from 1 to about 10. Most preferably, $R^{51}$ and $R^{52}$ are independently methyl, and $R^{53}$ is a linear or branched alkyl group having from about 8 to about 18 carbon atoms; or $R^{51}$ and $R^{52}$ are independently —$(R^{54}O)_x{}^5R^{55}$, $R^{53}$ is a linear or branched alkyl group having from about 8 to about 18 carbon atoms, $R^{54}$ in each of the $(R^{54}O)_x{}^5$ groups is ethylene or propylene, $R^{55}$ is hydrogen, and $x^5$ is an average number from 1 to about 5. Commercially available amine oxide surfactants include Chemoxide L70.

(g) dialkoxylated amines having the formula:

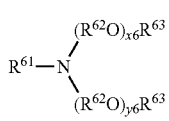

(7)

wherein $R^{61}$ is a linear or branched alkyl, linear or branched alkenyl, linear or branched alkynyl, aryl, or aralkyl group having from about 6 to about 30 carbon atoms, $R^{62}$ in each of the $(R^{62}O)_{x6}$ and the $(R^{62}O)_{y6}$ groups is independently $C_2$-$C_4$ alkylene, $R^{63}$ is hydrogen, or a linear or branched alkyl group having from 1 to about 4 carbon atoms and $x^6$ and $y^6$ are independently an average number from 1 to about 40. Preferably, $R^{61}$ is a linear or branched alkyl or linear or branched alkenyl group having from about 8 to about 30 carbon atoms, $R^{62}$ in each of the $(R^{62}O)_{x6}$ and the $(R^{62}O)_{y6}$ groups is independently $C_2$-$C_4$ alkylene, $R^{63}$ is hydrogen, methyl or ethyl, and $x^6$ and $y^6$ are independently an average number from 1 to about 20. More preferably, $R^{61}$ is a linear or branched alkyl group having from about 8 to about 25 carbon atoms, $R^{62}$ in each of the $(R^{62}O)_{x6}$ and the $(R^{62}O)_{y6}$ groups is independently ethylene or propylene, $R^{63}$ is hydrogen or methyl, and x and y are independently an average number from 1 to about 10. Even more preferably, $R^{61}$ is a linear or branched alkyl group having from about 8 to about 22 carbon atoms, $R^{62}$ in each of the $(R^{62}O)_{x6}$ and the $(R^{62}O)_{y6}$ groups is independently ethylene or propylene, $R^{63}$ is hydrogen or methyl, and $x^6$ and $y^6$ are independently an average number from 1 to about 5. Preferred commercially available dialkoxylated amines include Trymeen™ 6617 (from Cognis), Ethomeen™ C/12, C/15, C/20, C/25, T/12, T/15, T/20 and T/25 (from Akzo Nobel), and Genamin™ T-200 DG and T-200 NF (from Clariant).

(h) aminated alkoxylated alcohols having the following chemical structure:

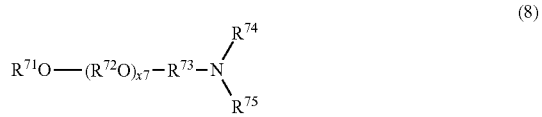

(8)

wherein $R^{71}$ is hydrogen or hydrocarbyl or substituted hydrocarbyl having from 1 to about 30 carbon atoms; $R^{72}$ in each of the $(R^{72}O)_{x7}$ and $(R^{72}O)_{y7}$ groups is independently $C_2$-$C_4$ alkylene; $R^{73}$ is hydrocarbylene or substituted hydrocarbylene having from 2 to about 30 carbon atoms; $R^{74}$ and $R^{75}$ are each independently hydrogen, hydrocarbyl or substituted hydrocarbyl having from 1 to about 30 carbon atoms, —$(R^{76})_{n7}$—$(R^{72}O)_y{}^7R^{77}$, or $R^{74}$ and $R^{75}$, together with the nitrogen atom to which they are attached, form a cyclic or heterocyclic ring; $R^{76}$ is hydrocarbylene or substituted hydrocarbylene having from 1 to about 30 carbon atoms; $R^{77}$ is hydrogen or a linear or branched alkyl group having 1 to about 4 carbon atoms, $n^7$ is 0 or 1, $x^7$ and $y^7$ are independently an average number from 1 to about 60. In this context, preferred $R^{71}$, $R^{73}$, $R^{74}$, $R^{75}$, and $R^{76}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^{71}$ is a linear or branched alkyl or linear or branched alkenyl group having from about 8 to about 25 carbon atoms, $R^{72}$ in each of the $(R^{72}O)_{x7}$ groups is independently $C_2$-$C_4$ alkylene, $R^{73}$ is a linear or branched alkylene group having from 2 to about 20 carbon atoms, $R^{74}$ and $R^{75}$ are each independently hydrogen or a linear or branched alkyl group having from 1 to about 6 carbon atoms, and $x^7$ is an average number from 1 to about 30. More preferably, $R^{71}$ is a linear or branched alkyl group having from about 12 to about 22 carbon atoms, $R^{72}$ in each of the $(R^{72}O)_{x7}$ groups is independently ethylene or propylene, $R^{73}$ is a linear or branched alkylene group having from 2 to about 6 carbon atoms, $R^{74}$ and $R^{75}$ are each independently hydrogen, methyl, or tris(hydroxymethyl)methyl, and $x^7$ is an average number from about 2 to about 30. Even more preferably, $R^{71}$ is a linear or branched alkyl group having from about 12 to about 18 carbon atoms, $R^{72}$ in each of the $(R^{72}O)_{x^7}$ groups is independently ethylene or propylene, $R^{73}$ is ethylene or propylene, $R^{74}$ and $R^{75}$ are each independently hydrogen, methyl or tris(hydroxymethyl)methyl, and $x^7$ is an average number from about 4 to about 20. Most preferably, $R^{71}$ is a linear or branched alkyl group having from about 12 to about 18 carbon atoms, $R^{72}$ in each of the $(R^{72}O)_{x7}$ groups is independently ethylene or propylene, $R^{73}$ is ethylene, $R^{74}$ and $R^{75}$ are methyl, and $x^7$ is an average number from about 4 to about 20. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah) and Surfonic™ AGM-550 from Huntsman.

Preferred anionic surfactants effective in forming potassium glyphosate formulations include:

(i) alkyl alkoxylated phosphates having the formula:

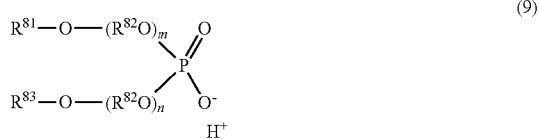

(9)

wherein $R^{81}$ and $R^{83}$ are independently a linear or branched alkyl, linear or branched alkenyl, linear or branched alkynyl, aryl, or aralkyl group having from about 4 to about 30 carbon atoms; $R^{82}$ in each of the $(R^{82}O)_m$ and the $(R^{82}O)_n$ groups is independently $C_2$-$C_4$ alkylene; and m and n are independently from 1 to about 30.

(j) alkyl alkoxylated phosphates having the formula:

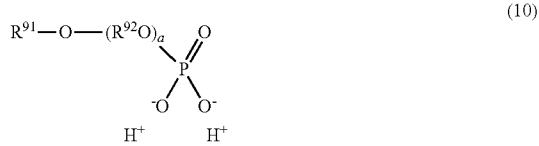

(10)

wherein $R^{91}$ is a linear or branched alkyl, linear or branched alkenyl, linear or branched alkynyl, aryl, or aralkyl group having from about 8 to about 30 carbon atoms; $R^{92}$ in each of the $(R^{92}O)_a$ groups is independently $C_2$-$C_4$ alkylene; and a is from 1 to about 30. Representative alkyl alkoxylated phosphates include oleth-10 phosphate, oleth-20 phosphate and oleth-25 phosphate.

In addition, nonionic surfactants or cosurfactants effective in such glyphosate formulations include:

(k) alkylpolyglycoside surfactants having the formula:

(11)

where $R^{101}$ is hydrogen or $C_{1-18}$ hydrocarbyl, $R^{104}$ is hydrogen or $C_{1-4}$ hydrocarbyl, q is 0 or 1, sug is (i) an open or cyclic structure derived from sugars, such as, for example, glucose or sucrose (referred to herein as a sugar unit), or (ii) a hydroxyalkyl, polyhydroxyalkyl or poly(hydroxyalkyl) alkyl group, u is an average number from 1 to about 2, and v is an integer from 1 to 3. This group includes several commercial surfactants collectively known in the art or referred to herein as "alkyl polyglucosides" or "APGs". Suitable examples are sold by Henkel as Agrimul™ PG-2069, Agrimul™ PG-2076 and Agrimul™ PG-2067.

(l) polysiloxane surfactants having the formula:

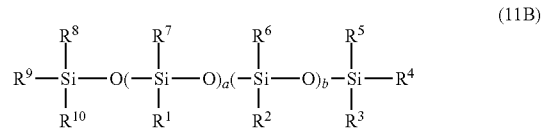

(11B)

wherein $R^1$ is $-C_nH_{2n}-O-(CH_2CH_2O)_m(CH_2CH(CH_3)O)_qX$, n is 0 to 6, a is 0 to about 100, b is 0 to about 10, m is 0 to about 30, q is 0 to about 30, X is hydrogen or a $C_{1-20}$ hydrocarbyl or $C_{2-6}$ acyl group, and $R^2$, $R^3$, $R^4$, $R^5$, $R^6$, $R^7$, $R^8$, $R^9$ and $R^{10}$ groups are independently substituted or unsubstituted $C_{1-20}$ hydrocarbyl or nitrogen containing groups. Generally, in preferred embodiments, n is 0 to 6, a is 1 to about 30, b is 0 to about 10, m is 0 to about 30, q is 0 to about 3, X is hydrogen or a $C_{1-6}$ hydrocarbyl or $C_{2-6}$ acyl group, and $R^2$, $R^3$, $R^4$, $R^5$, $R^6$, $R^7$, $R^8$, $R^9$ and $R^{10}$ groups are independently substituted or unsubstituted $C_{1-4}$ hydrocarbyl or nitrogen containing groups. In one preferred embodiment, the polysiloxane is a polyoxyethylene heptamethyl trisiloxane wherein $R^1$ is $-C_nH_{2n}-O-(CH_2CH_2O)_m(CH_2CH(CH_3)O)_qX$, n is 3 or 4, a is 1, b is 0, m is 1 to about 30, q is 0, X is hydrogen or a methyl, ethyl or acetyl group, and $R^2$, $R^3$, $R^4$, $R^5$, $R^6$, $R^7$, $R^8$, $R^9$ and $R^{10}$ groups are independently substituted or unsubstituted $C_{1-4}$ hydrocarbyl or nitrogen containing groups. In another preferred embodiment, a is 1 to 5, b is 0 to 10, n is 3 or 4, m is 1 to about 30, q is 0, X is hydrogen or a methyl, ethyl or acetyl group, and $R^2$, $R^3$, $R^4$, $R^5$, $R^6$, $R^7$, $R^8$, $R^9$ and $R^{10}$ are methyl groups. In another preferred embodiment, a is 1 to 5, b is 0 to 10, n is 3 or 4, m is 4 to 12, q is 0, X is hydrogen or a methyl or acetyl group, $R^2$, $R^3$, $R^4$, $R^5$, $R^6$, $R^7$, $R^8$, $R^9$ and $R^{10}$ are methyl groups. In a more preferred embodiment, a is 1, b is 0, n is 3 or 4, m is 1 to about 30, b is 0, X is hydrogen or a methyl, ethyl or acetyl group, and $R^2$, $R^3$, $R^4$, $R^5$, $R^6$, $R^7$, $R^8$, $R^9$ and $R^{10}$ are methyl groups. In a further preferred embodiment, a is 1, b is 0, n is 3, m is 8, b is 0, X is methyl and $R^2$, $R^3$, $R^4$, $R^5$, $R^6$, $R^7$, $R^8$, $R^9$ and $R^{10}$ are methyl groups. Trisiloxanes of the above formula are generally described in product literature of Crompton Corporation and in U.S. Pat. No. 3,505,377. Several of such trisiloxanes are ethoxylated organosilicone wetting agents available from Crompton Corporation as Silwet® silicone glycol copolymers. Both liquid organosilicones and dry organosilicones can be used in the surfactant composition; both are included within the scope of the invention. More preferred trisiloxanes are those sold commercially in the United States or elsewhere by Crompton Corporation as Silwet® L-77, Silwet® 408 and Silwet® 800, by Dow-Corning as Sylgard® 309, by Exacto, Inc., as Qwikwet® 100, and by Goldschmidt as Breakthru S-240. In the most preferred polyoxyethylene heptamethyl trisiloxanes, $R^2$ is hydrogen.

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 EO groups. Preferred alkylamine compounds include $C_6$ to $C_{12}$ alkylamines having 0 to 2 EO groups. Similarly, etheramine compounds having 4 to 12 carbons and 0 to about 5 EO groups, as well as the corresponding quaternary ammonium compounds, also enhance the compatibility of such formulations. In one embodiment, the compounds which enhance the compatibility of such surfactants include:

(m) amines or quaternary ammonium salts having the formula:

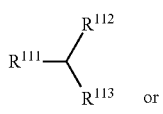
(12)

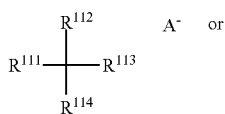
(13)

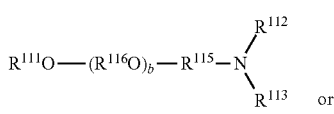
(14)

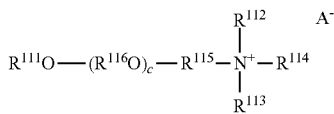
(15)

wherein $R^{111}$ is linear or branched alkyl or aryl having from about 4 to about 16 carbon atoms, $R^{112}$ is hydrogen, methyl, ethyl, or —$(CH_2CH_2O)_dH$, $R^{113}$ is hydrogen, methyl, ethyl, or —$(CH_2CH_2O)_eH$ wherein the sum of d and e is not more than about 5; $R^{114}$ is hydrogen or methyl; $R^{116}$ in each of the $(R^{116}O)_c$ groups is independently $C_2$-$C_4$ alkylene; $R^{115}$ is hydrocarbylene or substituted hydrocarbylene having from 2 to about 6 carbon atoms; and $A^-$ is an agriculturally acceptable anion.

In aqueous concentrated formulations of the present invention, the ratio (by weight) of the glyphosate a.e. to the surfactant is typically in the range of from about 1:1 to about 20:1, preferably from about 2:1 to about 10:1, more preferably from about 2:1 to about 8:1, still more preferably from about 2:1 to about 6:1, still more preferably from about 3:1 to about 6:1, and still more preferably about 4.5:1 to 6:1.

In another embodiment, preferably, the surfactant of the compositions of the invention comprises a first surfactant component which includes one or more surfactants selected from the group consisting of:

(a) ether amines having formula (5) described above in paragraph (e);

(b) dialkoxylated amines having formula (7) described above in paragraph (g); and (c) aminated alkoxylated alcohols having formula (8) described above in paragraph (h). The most preferred surfactants are those which provide a cloud point greater than about 60° C. in a composition having a glyphosate loading of at least about 480 g a.e./l.

In a further embodiment, preferably, the surfactant of the compositions of the invention comprises a first surfactant component as described in detail above and additionally a second surfactant component which includes one or more surfactant(s) selected from the group consisting of:

(a) secondary or tertiary amines having formula (1) described above in paragraph (a);

(b) dialkoxylated quaternary ammonium salts having formula (2) described above in paragraph (b);

(c) monoalkoxylated quaternary ammonium salts having formula (3) described above in paragraph (c);

(d) quaternary ammonium salts having formula (4) described above in paragraph (d);

(e) amine oxides having formula (6) described above in paragraph (e);

(f) alkyl alkoxylated phosphates having formula (9) described above in paragraph (i);

(g) alkyl alkoxylated phosphates having formula (10) described above in paragraph (j);

(h) alkylpolyglycosides having formula (11) described above in paragraph (k); and (i) amines or quaternary ammonium salts having formulae (12)-(15) described above in paragraph (l).

In yet another embodiment, more preferably, the second surfactant component is selected from the group consisting of:

(a) alkylpolyglycosides having formula (11) described above in paragraph (k); and (b) amines or quaternary ammonium salts having formulae (12)-(15) described above in paragraph (l).

In an embodiment of the invention, the density of the formulation of the invention is preferably at least 1.210 grams/liter, more preferably at least about 1.215, 1.220, 1.225, 1.230, 1.235, 1.240, 1.245, 1.250, 1.255, 1.260, 1.265, 1.270, 1.275, 1.280, 1.285, 1.290, 1.295, 1.300, 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.410, 1.415, 1.420, 1.425, 1.430, 1.435, 1.440, 1.445, or 1.450 grams/liter.

As further discussed herein, other additives, adjuvants, or ingredients may be introduced into the formulations of the present invention to improve certain properties of the resulting formulations. Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. Suitable solubilizers for use with the novel formulations of the present invention include, for example, cocoamine (Armeen C), dimethylcocoamine (Arquad DMCD), cocoammonium chloride (Arquad C), PEG 2 cocoamine (Ethomeen C12), PEG 5 tallowamine (Ethomeen T15), and PEG 5 cocoamine (Ethomeen C15), all of which are manufactured by Akzo Nobel (California). Additional excipient ingredients may include conventional formulation additives such as dyes, thickeners, crystallization inhibitors, antifreeze agents (e.g., glycols, such as ethylene glycol, or polyethylene glycols such as polyethylene glycol 200, 400, 600, 1500, 4000 or 6000), foam moderating agents (e.g., Antifoam™ or Y-14088 Antifoam™, both available from Crompton Corporation), antidrift agents, compatibilizing agents, antioxidants (e.g., ascorbic acid and sodium sulfite, in order for example to prevent the formation of a nitrosamine), other co-solvents (e.g., N-methylpyrrolidone, DMSO, DMF, propylene carbonate, or ethylene glycol), or some other agent added to lessen or overcome antagonism associated with hard water (e.g., ammonium sulfate, EDTA or a polymeric water conditioner, such as a polyacrylic acid).

Other components such as solvents and organic acids may be added to enhance concentrate stability. These additives generally function to increase solubility or dispersability of the surfactants in the aqueous carrier thus enabling the formulation of robust concentrates exhibiting enhanced thermal and pH stability, reduced viscosity, and high glyphosate loading. Non-limiting examples of water soluble solvents include acetates, $C_{1-6}$ alkanols, $C_{1-6}$ diols, $C_{1-6}$ alkyl ethers of alkylene glycols and polyalkylene glycols, and mixtures thereof. The alkanol can be selected from methanol, ethanol, n-propanol, isopropanol, the various positional isomers of butanol, pentanol, and hexanol, and mixtures thereof. It may also be possible to utilize in addition to, or in place of, said alkanols, the diols such as methylene, ethylene, diethylene, propylene, dipropylene, and butylene glycols, and mixtures thereof, and including polyalkylene glycols. These components are generally employed in dispersion-effective or solubilizing effective amounts. Suitable organic acids include, among others, acetic, dichloroacetic, citric, malic, oxalic, salicylic and tartaric. Effective concentrations of organic acids are generally between about 0.1 wt % and 5 wt %.

Although additional herbicides can be included in the compositions of the invention other than the glyphosate and auxin herbicides, it is preferred that the glyphosate and the auxin herbicides are the only herbicides in the composition.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl (—$CH_2OH$), and hydroxyethyl (—$C_2H_4OH$), bis(hydroxymethyl)methyl (—$CH(CH_2OH)_2$), and tris(hydroxymethyl)methyl (—$C(CH_2OH)_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The term "pesticide" includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives, the delivery of which to the target may expose dermal and especially ocular tissue to the pesticide. Such exposure can arise by drift of the pesticide from the delivery means to the person performing the application of the pesticide or being present in the vicinity of an application.

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

By "storage-stable," in the context of an aqueous concentrate composition of glyphosate salt further containing a surfactant and auxin herbicide, is meant not exhibiting phase separation on exposure to temperatures up to about 50° C., and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate SL formulation. Ideally the cloud point should be 60° C. or more, and the composition should withstand temperatures as low as about −10° C., preferably as low as about −20° C., more preferably as low as about −30 C, for up to about 7 days without phase separation (i.e., without separation of frozen water or solid insoluble surfactant from the composition) and without crystal growth (even in the presence of seed crystals of the glyphosate salt).

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. The herbicidal effectiveness data set forth herein report "control" as a percentage following a standard procedure in the art which reflects a visual assessment of plant mortality and growth reduction by comparison with untreated plants, made by technicians specially trained to make and record such observations. In all cases, a single technician makes all assessments of percent control within any one experiment or trial. Such measurements are relied upon and regularly reported by Monsanto Company in the course of its herbicide business.

Examples

The spray compositions of the following examples contain an exogenous chemical, such as glyphosate salt as indicated, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

In the following Examples illustrative of the invention, greenhouse and field tests were conducted to evaluate the relative herbicidal effectiveness of glyphosate compositions. Standard compositions included for comparative purposes include the following:

STD1: 725 g/l of glyphosate potassium salt in aqueous solution with no added surfactant.

STD2: 50% by weight of glyphosate IPA salt in aqueous solution together with a surfactant. This formulation is sold by Monsanto Company under the ROUNDUP ULTRAMAX® trademark.

STD3: 570 g/l of glyphosate IPA salt in an aqueous solution with no added surfactant.

Various excipients were used in compositions of the examples. They may be identified as follows.

Cationic Surfactants:

| CIS1 | Witcamine TAM105 | Ethoxylated (10.5) tallowamine |
|---|---|---|
| CIS2 | 3151 blend | 55% Ethoxylated (10.5) tallowamine and 45% Ethoxylated (2) cocoamine |

-continued

| | | |
|---|---|---|
| CIS3 | Surfonic T-15 | PEG 15 tallow amine |
| CIS4 | Witcamine 302 | PEG 2 cocoamine |
| CIS5 | Witcamine 305 | PEG 5 cocoamine |
| CIS6 | Formulation E1 of Reissue Pat. No. RE. 37,866 | $C_{12-14}$ alkoxylated (1 PO) propylamine (5EO) ethoxylate |
| CIS7 | Armeen C | coco ($C_{12}$-$C_{18}$ unsaturated) primary amine |
| CIS8 | Ethoquad T25 | tallow ethoxylate (15EO) quaternary ammonium chloride |
| CIS9 | MON 0818 | polyoxyethylene tallowamine |
| CIS10 | | $C_{18}$NMe(EO)7.5H |
| CIS11 | 7164 blend | 54% 4.5EO tallowamine ethoxylate, 23% 10 EO tallowamine ethoxylate, and 23% dipropylene glycol |
| CIS12 | Witcamine TAM 45 | 4.5 EO tallowamine ethoxylate |
| CIS13 | Arquad T-50PG | tallowtrimethylammonium chloride in propylene glycol |
| CIS14 | Arquad SV-60PG | soyaalkyltrimethyl ammonium chloride |
| CIS15 | Tomah E-17-5 | poly(5)oxyethylene isodecyl oxypropylamine |

Nonionic Surfactants:

| | | |
|---|---|---|
| NIS1 | Hetoxol CS20 | $C_{16-18}$ alcohol ethoxylate (20EO) |
| NIS2 | Agrimul PG 2067 | Alkylpolyglucoside (Cognis) |
| NIS3 | | $C_{16-18}$ alcohol ethoxylate (20EO) |
| NIS4 | Witconol IS 100 | PEG 10EO iso $C_{18}$ alcohol |
| NIS5 | Silwet L-77 | silicone-polyether copolymer |
| NIS6 | Brij 56 | stearyl alcohol ethoxylate (10EO) |
| NIS7 | ADMOX SC1485 | myristyl dimethyl amine oxide |
| NIS8 | | 20 EO linear $C_{16-18}$ alcohol ethoxylate |
| NIS9 | Emulgin L | ceteareth propoxylate (2PO) ethoxylate (9EO) |
| NIS10 | | alkoxylated alcohol |
| NIS11 | | alkoxylated alcohol |

Other Components:

| | | |
|---|---|---|
| OTH1 | Di-ammonium Oxalate | |
| OTH2 | Propylene Glycol | |
| OTH3 | Oxalic Acid | |
| OTH4 | Sodium Sulfite | |
| OTH5 | Agnique DF6889 | Silicone dispersion antifoam |
| OTH6 | octyl amine | |
| OTH7 | tetrahydrofuryl alcohol | |
| OTH8 | Isopar L | paraffinic oil |
| OTH9 | dipropylene glycol | |
| OTH10 | diethylene glycol | |
| OTH11 | NaCl | |
| OTH12 | KOH | |
| OTH13 | glycerin | |
| OTH14 | phosphoric acid | |
| OTH15 | dimethyl amine | |
| OTH16 | N-decyl amine | |
| OTH17 | diethyl amine | |
| OTH18 | isopropyl alcohol | |

The following greenhouse testing procedure was used for evaluating compositions of the Examples to determine herbicidal effectiveness, except where otherwise indicated.

Seeds of the plant species indicated were planted in 88 mm square pots in a soil mix which was previously sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 29 C during the day and about 21 C during the night. Plants were sub-irrigated throughout the test to ensure adequate soil moisture levels.

Pots were assigned to different treatments in a fully randomized experimental design with 6 replications. A set of pots was left untreated as a reference against which the effects of a treatment could later be evaluated.

Application of glyphosate compositions was made by spraying with a track sprayer fitted with a 9501E tapered flat fan spray tip calibrated to deliver a spray volume of 93 liters per hectare (l/ha) at a pressure of 165 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. The reported % control values represent the average for all replicates of each treatment.

Example 1

The effect of glyphosate, 2,4-D, combinations of 2,4-D and glyphosate and combinations of all of the above with oxalic acid on velvetleaf was tested. Aqueous concentrate compositions were prepared containing potassium glyphosate salt, reported in g a.e./liter, and excipient ingredients as shown in Table 1a. The 806D0T, 806E7S, 806F4Q and 806G3B formulations contained 62 grams acid equivalent per liter. Formulations 806A2D, 806B9H, 806C5Z, 806F4Q and 806G3B contained the IPA salt of 2,4-D measured in grams acid equivalent per liter.

TABLE 1a

| Comp. | Gly. | 2,4-D | Cmpnt. 2 | wt % | Cmpnt. 3 | wt % | Cmpnt. 4 | wt % |
|---|---|---|---|---|---|---|---|---|
| 806A2D | — | 60.0 | — | | — | | — | — |
| 806B9H | — | 60.0 | CIS6 | 0.75 | NIS2 | 1.0 | — | — |
| 806C5Z | — | 60.0 | CIS6 | 0.75 | NIS2 | 1.0 | OTH3 | 0.30 |
| 806D0T | K | — | CIS6 | 0.75 | NIS2 | 1.0 | — | — |
| 806E7S | K | — | CIS6 | 0.75 | NIS2 | 1.0 | OTH3 | 0.30 |
| 806F4Q | K | 2.0 | CIS6 | 0.75 | NIS2 | 1.0 | — | 0.75 |
| 806G3B | K | 2.0 | CIS6 | 0.75 | NIS2 | 1.0 | OTH3 | 0.30 |
| 765K4S | K | — | CIS5 | 9.0 | NIS4 | 4.0 | CIS7 | 1.0 |

The compositions of Table 1a and comparative compositions STD1 and STD2, were applied to velvetleaf (*Abutilon theophrasti*, ABUTH) plants. Results, averaged for all replicates of each treatment, are shown in Table 1b.

TABLE 1b

| Composition | Glyphosate Application Rate (g a.e./ha) | ABUTH % inhibition |
|---|---|---|
| 806A2D | 100, 200, 300, 400 | 59.2, 75.8, 77.5, 80.0 |
| 806B9H | 100, 200, 300, 400 | 66.7, 75.0, 80.0, 80.0 |
| 806C5Z | 100, 200, 300, 400 | 75.0, 78.3, 80.0, 82.5 |
| 806D0T | 100, 200, 300, 400 | 24.2, 59.2, 85.0, 88.3 |
| 806E7S | 100, 200, 300, 400 | 77.5, 87.5, 96.0, 98.0 |
| 806F4Q | 100, 200, 300, 400 | 25.0, 75.0, 80.8, 86.7 |
| 806G3B | 100, 200, 300, 400 | 68.3, 89.2, 95.5, 97.3 |
| 765K4S | 100, 200, 300, 400 | 16.7, 63.3, 85.0, 90.0 |
| STD1 | 100, 200, 300, 400 | 0.0, 1.7, 44.2, 77.5 |
| STD2 | 100, 200, 300, 400 | 13.3, 81.7, 90.0, 95.0 |

The order of efficacy for ABUTH % inhibition was 806E7S>806G3B>806C5Z>806B9H>806A2D>STD2>806F4Q>806D0T>765K4S>STD1.

Example 2

The effect of combinations of potassium glyphosate and 2,4-D with or without oxalic acid on velvetleaf was tested. Aqueous concentrate compositions were prepared containing potassium glyphosate salt, reported in g a.e./liter, and excipient ingredients as shown in Table 2a. The 820A9T, 820C1Z, 820D6Q, 820E3F, 820F0G and 820H7D formulations contained 62 grams acid equivalent per liter. Formulation 820B4H contained the IPA salt of 2,4-D measured in grams acid equivalent per liter.

TABLE 2a

| Comp. | Gly. | 2,4-D | Cmpnt. 2 | wt % | Cmpnt. 4 | wt % | Cmpnt. 4 | wt % |
|---|---|---|---|---|---|---|---|---|
| 820A9T | K | — | CIS6 | 0.75 | NIS2 | 1.00 | — | — |
| 820B4H | — | 60.0 | CIS6 | 0.75 | NIS2 | 1.00 | — | — |
| 820C1Z | K | 2.0 | CIS6 | 0.75 | NIS2 | 1.00 | OTH3 | 0.30 |
| 820D6Q | K | 2.0 | CIS6 | 0.75 | NIS2 | 1.00 | — | — |
| 820E3F | K | 6.0 | CIS6 | 0.75 | NIS2 | 1.00 | OTH3 | 0.30 |
| 820F0G | K | 6.0 | CIS6 | 0.75 | NIS2 | 1.00 | — | — |
| 820G5J | K | 4.0 | CIS6 | 0.75 | NIS2 | 1.00 | OTH3 | 0.60 |
| 820H7D | K | 6.0 | CIS6 | 0.75 | NIS2 | 1.00 | OTH3 | 0.60 |

The compositions of Table 2a and comparative compositions STD1 and STD2 were applied to velvetleaf (*Abutilon theophrasti*, ABUTH) plants. Results at 4 days after treatment (4DAT) and 14 days after treatment (14DAT), averaged for all replicates of each treatment, are shown in Table 2b.

TABLE 2b

| Comp. | Glyphosate Application Rate (ga.e./ha) | ABUTH % inhibition (4DAT) | ABUTH % inhibition (14DAT) |
|---|---|---|---|
| 820A9T | 150, 250, 400, 800 | 5.0, 5.0, 10.0, 10.0 | 40.8, 75.0, 84.2, 93.8 |
| 820B4H | 150, 250, 400, 800 | 20.0, 25.0, 35.0, 40.0 | 66.7, 76.7, 80.8, 81.7 |
| 820C1Z | 150, 250, 400, 800 | 5.0, 5.0, 5.0, 10.0 | 79.2, 85.0, 95.0, 99.2 |
| 820D6Q | 150, 250, 400, 800 | 5.0, 5.0, 5.0, 10.0 | 25.8, 76.7, 85.0, 91.7 |
| 820E3F | 150, 250, 400, 800 | 5.0, 5.0, 10.0, 15.0 | 78.3, 80.8, 90.5, 97.3 |
| 820F0G | 150, 250, 400, 800 | 5.0, 5.0, 10.0, 15.0 | 22.5, 65.0, 83.3, 94.8 |
| 820G5J | 150, 250, 400, 800 | 10.0, 15.0, 20.0, 25.0 | 79.2, 85.0, 93.8, 100.0 |
| 820H7D | 150, 250, 400, 800 | 10.0, 15.0, 20.0, 25.0 | 79.2, 85.0, 96.2, 99.3 |
| STD1 | 150, 250, 400, 800 | 0.0, 5.0, 5.0, 5.0 | 0.0, 26.7, 70.8, 84.2 |
| STD2 | 150, 250, 400, 800 | 5.0, 5.0, 10.0, 10.0 | 70.0, 85.0, 90.0, 98.7 |

The order of efficacy for ABUTH % inhibition was 820H7D>820C1Z>820G5J>820E3F>STD2>820B4H>820A9T>765K4S>820D6Q>820F0G>STD1.

Example 3

The effect of tank mixtures of NH$_4$-oxalate with glyphosate package premix formulations of RT Master™ and Field Master™ on velvetleaf and barnyardgrass was tested. Aqueous tank mix compositions were prepared containing Roundup® UltraMax, RT Master™ and Field Master™ along with NH$_4$-oxalate at three glyphosate a.e.:oxalate ratios (2:1, 10:1 and 30:1) these compositions and excipient ingredients are shown in Table 3a.

TABLE 3a

| Composition | Glyphosate (g a.e./L) | 2,4-D (g a.e./L) | Gly:Oxalic Acid Ratio |
|---|---|---|---|
| UltraMax 21 | 445 | — | 2:1 |
| UltraMax 101 | 445 | — | 10:1 |
| UltraMax 301 | 445 | — | 30:1 |
| RT Master 21 | 360 | 38.6 | 2:1 |
| RT Master 101 | 360 | 38.6 | 10:1 |
| RT Master 301 | 360 | 38.6 | 30:1 |
| Field Master 21 | 68 | — | 2:1 |
| Field Master 101 | 68 | — | 10:1 |
| Field Master 301 | 68 | — | 30:1 |

The compositions of Table 3a and comparative compositions STD1, STD2, RT Master™ and Field Master™ were applied to velvetleaf (*Abutilon theophrasti*, ABUTH) and Japanese millet (*Echinochloa crus-galli* var. *frumentae*, ECHCF) plants. Results at 5 days after treatment (5DAT) and 16 days after treatment (16DAT), averaged for all replicates of each treatment, are shown in Table 3b.

TABLE 3b

| Composition | Glyphosate App. Rate (g a.e./ha) | ABUTH % inhibition (5DAT) | ABUTH % inhibition (16DAT) | ECHCF % inhibition (5DAT) | ECHCF % inhibition (16DAT) |
|---|---|---|---|---|---|
| UltraMax 21 | 75, 100, 200 | 0.0, 0.0, 0.0 | 78.3, 88.3, 97.5 | 0.0, 0.0, 0.0 | 61.7, 80.8, 94.8 |
| UltraMax 101 | 75, 100, 200 | 0.0, 0.0, 0.0 | 70.8, 85.8, 97.8 | 0.0, 0.0, 0.0 | 61.7, 79.2, 97.5 |
| UltraMax 301 | 75, 100, 200 | 0.0, 0.0, 0.0 | 65.8, 80.8, 96.0 | 0.0, 0.0, 0.0 | 55.0, 80.8, 92.8 |
| RT Master 21 | 75, 100, 200 | 0.0, 2.5, 5.0 | 75.0, 83.3, 94.7 | 0.0, 0.0, 0.0 | 65.0, 85.0, 96.2 |
| RT Master 101 | 75, 100, 200 | 0.0, 3.3, 5.0 | 66.7, 77.5, 91.7 | 0.0, 0.0, 0.0 | 63.3, 82.5, 94.8 |
| RT Master 301 | 75, 100, 200 | 0.0, 4.2, 5.0 | 54.2, 75.8, 90.0 | 0.0, 0.0, 0.0 | 60.0, 80.8, 93.5 |
| Field Master 21 | 75, 100, 200 | 3.3, 13.3, 32.5 | 76.7, 88.3, 90.5 | 0.0, 7.5, 16.7 | 48.3, 60.0, 61.7 |
| Field Master 101 | 75, 100, 200 | 2.5, 10.8, 26.7 | 65.0, 76.7, 80.0 | 0.0, 4.2, 11.7 | 35.0, 52.5, 54.2 |
| Field Master 301 | 75, 100, 200 | 1.7, 6.7, 16.7 | 48.3, 74.2, 79.2 | 0.0, 1.7, 9.2 | 20.8, 47.5, 50.0 |
| RT Master™ | 75, 100, 200 | 2.5, 4.2, 5.0 | 47.5, 61.7, 77.5 | 0.0, 0.0, 0.0 | 55.0, 78.3, 91.2 |
| Field Master™ | 75, 100, 200 | 4.2, 16.7, 48.3 | 40.8, 54.2, 84.8 | 0.0, 8.3, 23.3 | 27.5, 49.2, 50.0 |
| STD1 | 75, 100, 200 | 0.0, 0.0, 0.0 | 6.7, 45.8, 64.2 | 0.0, 0.0, 0.0 | 3.3, 30.0, 49.2 |
| STD2 | 75, 100, 200 | 0.0, 0.0, 0.0 | 40.8, 75.8, 86.3 | 0.0, 0.0, 0.0 | 58.3, 77.5, 91.5 |

The order of efficacy averaged across application rates for the ABUTH % inhibition was UltraMax 21>Field Master 21>UltraMax 101>RT Master 21>UltraMax 301>RT Master 101>Field Master 101>RT Master 301>STD2>Field Master 301>RT Master>Field Master>STD1. The order of efficacy averaged across application rates for ECHF % inhibition was RT Master 21>RT Master 101>UltraMax 101>UltraMax 21>RT Master 301>UltraMax 301>STD 3>RT Master>Field Master 21>Field Master 101>Field Master>Field Master 301>STD1. The order of efficacy averaged across application rates for both ABUTH and ECHCF combined was UltraMax 21>RT Master 21>UltraMax 101>RT Master 101>UltraMax 301>RT Master 301>STD2>Field Master 21>RT Master>Field Master 101>Field Master 301>Field Master>STD1.

Example 4

The effect of tank mixtures of NH$_4$-oxalate with glyphosate premix formulations of Roundup® RTU and Fallow Master® on velvetleaf and barnyardgrass was tested. Aqueous tank mix compositions were prepared containing Roundup® UltraMax, Roundup® RTU and Fallow Master® along with NH$_4$-oxalate at three glyphosate a.e.:oxalate ratios (2:1, 10:1 and 30:1) these compositions and excipient ingredients are shown in Table 4a.

TABLE 4a

| Composition | Gly. | Component 2 (g a.e./L) | Gly:Oxalic Acid Ratio |
|---|---|---|---|
| UltraMax 21 | 445 gae/L | — | 2:1 |
| UltraMax 101 | 445 gae/L | — | 10:1 |
| UltraMax 301 | 445 gae/L | — | 30:1 |
| RTU 21 | 1.9 wt % ae | (diquat) | 2:1 |
| RTU 101 | 1.9 wt % ae | (diquat) | 10:1 |
| RTU 301 | 1.9 wt % ae | (diquat) | 30:1 |
| Fallow Master ® 21 | 197 gae/L | 46 (dicamba) | 2:1 |
| Fallow Master 101 | 197 gae/L | 46 (dicamba) | 10:1 |
| Fallow Master 301 | 197 gae/L | 46 (dicamba) | 30:1 |

The compositions of Table 4a and comparative compositions Roundup® RTU, Fallow Master®, STD1 and STD2 were applied to velvetleaf (*Abutilon theophrasti*, ABUTH) and Japanese millet (*Echinochloa crus-galli* var. *frumentae*, ECHCF) plants. Results at 14 days after treatment (14DAT), averaged for all replicates of each treatment, are shown in Table 4b.

TABLE 4b

| Composition | Glyphosate Application Rate (g a.e./ha) | ABUTH % inhibition (14DAT) | ECHCF % inhibition (14DAT) |
|---|---|---|---|
| UltraMax 21 | 75, 100, 200 | 51.7, 80.0, 90.0 | 67.5, 68.3, 75.8 |
| UltraMax 101 | 75, 100, 200 | 51.7, 76.7, 85.8 | 64.2, 68.3, 73.3 |
| UltraMax 301 | 75, 100, 200 | 46.7, 67.5, 85.0 | 60.0, 68.3, 71.7 |
| RTU 21 | 75, 100, 200 | 23.3, 27.5, 38.3 | 1.7, 6.7, 56.7 |
| RTU 101 | 75, 100, 200 | 5.0, 10.0, 38.3 | 0.8, 7.5, 50.0 |
| RTU 301 | 75, 100, 200 | 4.2, 10.0, 32.5 | 4.2, 17.5, 63.3 |
| Fallow Master ® 21 | 75, 100, 200 | 68.3, 78.3, 87.5 | 65.0, 67.5, 89.7 |
| Fallow Master 101 | 75, 100, 200 | 66.7, 81.7, 85.0 | 65.8, 67.5, 90.0 |
| Fallow Master 301 | 75, 100, 200 | 66.7, 78.3, 85.8 | 65.0, 70.8, 91.8 |
| Roundup RTU | 75, 100, 200 | 5.8, 16.7, 35.0 | 5.8, 21.7, 61.7 |
| Fallow Master | 75, 100, 200 | 60.0, 70.0, 84.2 | 64.2, 66.7, 81.7 |
| STD1 | 75, 100, 200 | 3.3, 7.5, 31.7 | 20.8, 40.8, 59.2 |
| STD2 | 75, 100, 200 | 10.8, 40.0, 76.7 | 64.2, 65.0, 72.5 |

The order of efficacy averaged across application rates for the ABUTH % inhibition was FallowMaster 21>Fallow- Master 101>FallowMaster 301>UltraMax 21>UltraMax 101>FallowMaster>UltraMax 301>STD2>RTU 21>Roundup RTU>RTU 101>STU 301>STD1. The order of efficacy averaged across application rates for ECHF % inhibition was FallowMaster 301>FallowMaster 101>FallowMaster 21>FallowMaster>UltraMax 21>UltraMax 101>STD 3>UltraMax 301>STD1>Roundup RTU>RTU 301>RTU 21>RTU 101. The order of efficacy averaged across application rates for both ABUTH and ECHCF combined was FallowMaster 301>FallowMaster 101>FallowMaster 21>UltraMax 21>FallowMaster>UltraMax 101>UltraMax 301>STD2>STD1>RTU 21>Roundup RTU>RTU 301>RTU 101.

Example 5

The effect of combinations of potassium glyphosate and 2,4-D and isopropylamine glyphosate on pitted morningglory (IPOLA) and cocklebur (XANST) was tested. Aqueous concentrate compositions were prepared containing 360 g a.e./L potassium glyphosate salt, amounts of 2,4-D are reported in wt % a.e. and excipient ingredients as shown in Table 5a.

TABLE 5a

| Comp. | Gly. | 2,4-D | Cmpnt. 2 | wt % | Cmpnt. 3 | wt % |
|---|---|---|---|---|---|---|
| 100B2T | K | 1.60 | CIS6 | 9.2 | — | — |
| 085A9K | K | 1.60 | CIS6 | 9.1 | — | — |
| 501A0X | K | 1.66 | CIS2 | 9.2 | — | — |
| 501B4S | K | 1.82 | CIS2 | 9.1 | — | — |
| 047B7Z | K | 3.13 | CIS6 | 9.2 | OTH6 | 2.16 |
| 059A3D | K | 3.13 | CIS2 | 9.2 | OTH6 | 2.20 |

The compositions of Table 5a and comparative composition RT Master™ were applied to pitted morningglory (IPOLA) and cocklebur (XANST) plants. Results at 10 days after treatment (10DAT), averaged for all replicates of each treatment, are shown in Table 5b.

TABLE 5b

| Composition | Glyphosate Application Rate (g a.e./ha) | XANST % inhibition (10DAT) | IPOLA % inhibition (10DAT) |
|---|---|---|---|
| 100B2T | 100, 200, 300, 400 | 38.8, 68.8, 73.8, 70.0 | 60.0, 76.3, 81.3, 93.8 |
| 085A9K | 100, 200, 300, 400 | 42.5, 65.0, 83.8, 83.8 | 60.0, 77.5, 78.8, 83.8 |
| 501A0X | 100, 200, 300, 400 | 56.3, 71.3, 82.5, 91.3 | 65.0, 78.8, 82.5, 85.0 |

TABLE 5b-continued

| Composition | Glyphosate Application Rate (g a.e./ha) | XANST % inhibition (10DAT) | IPOLA % inhibition (10DAT) |
|---|---|---|---|
| 501B4S | 100, 200, 300, 400 | 58.8, 65.0, 76.3, 85.0 | 62.5, 83.8, 80.0, 91.3 |
| 047B7Z | 100, 200, 300, 400 | 58.8, 73.8, 87.5, 97.5 | 86.3, 86.3, 90.0, 93.8 |
| 059A3D | 100, 200, 300, 400 | 70.8, 79.5, 88.0, 90.0 | 72.5, 88.8, 87.5, 97.5 |
| RT Master ™ | 100, 200, 300, 400 | 53.8, 69.5, 78.5, 83.3 | 75.0, 83.8, 92.5, 88.8 |

The order of efficacy averaged across application rates for the XANST % inhibition was 059A3D>047B7Z>501A0X>501B4S>RT Master™>085A9K>100B2T. The order of efficacy averaged across application rates for IPOLA % inhibition was 047B7Z>059A3D>RT Master™>501B4S>100B2T>501A0X>085A9K. The order of efficacy averaged across application rates for both XANST and IPOLA combined was 059A3D>047B7Z>RT Master™>501A0X>501B4S>085A9K>100B2T.

Example 6

The effect of combinations of potassium glyphosate and 2,4-D and isopropylamine glyphosate on pitted morningglory (IPOLA) plants was tested. Aqueous concentrate compositions were prepared containing 480 g a.e./L potassium glyphosate salt, 2,4-D reported in wt % a.e, and excipient ingredients as shown in Table 6a.

TABLE 6a

| Comp. | Gly. | 2,4-D | Cmpnt. 2 | wt % |
|---|---|---|---|---|
| 506A2T | K | 0.72 | CIS2 | 7.25 |
| 506B9Z | K | 0.71 | CIS2 | 7.25 |
| 510A4H | K | 0.60 | CIS6 | 7.60 |
| 510B8V | K | 0.60 | CIS6 | 7.60 |
| 508A1B | K | 0.72 | CIS2 | 7.60 |
| 508B0G | K | 0.72 | CIS2 | 7.60 |
| 503B5P | K | 0.66 | CIS6 | 9.10 |
| 504A3L | K | 0.65 | CIS6 | 9.10 |
| 504B2I | K | 0.74 | CIS2 | 9.10 |
| 505A6S | K | 0.72 | CIS2 | 9.10 |

The compositions of Table 6a and comparative compositions RT Master™ and STD2 were applied to pitted morningglory (IPOLA). Results at 5 days after treatment (5DAT) and 12 days after treatment (12DAT), averaged for all replicates of each treatment, are shown in Table 6b.

TABLE 6b

| Comp. | Glyphosate App. Rate (g a.e./ha) | IPOLA % inhibition (5DAT) | IPOLA % inhibition (11DAT) | IPOLA % inhibition (12DAT) | XANST % inhibition (11DAT) |
|---|---|---|---|---|---|
| 506A2T | 100, 200, 400 | 30.0, 67.5, 75.0 | 25.0, 72.5, 81.7 | 30.0, 75.0, 90.0 | 60.0, 71.3, 86.3 |
| 506B9Z | 100, 200, 400 | 33.8, 47.5, 80.0 | 66.3, 72.5, 86.7 | 33.8, 71.3, 90.0 | 65.0, 77.5, 81.3 |
| 510A4H | 100, 200, 400 | 61.3, 58.8, 85.0 | 22.5, 72.5, 80.0 | 58.8, 73.8, 92.5 | 55.0, 77.5, 78.8 |
| 510B8V | 100, 200, 400 | 41.3, 65.0, 78.8 | 30.0, 67.5, 83.4 | 45.0, 77.5, 90.5 | 45.0, 60.0, 92.5 |
| 508A1B | 100, 200, 400 | 35.0, 77.5, 80.0 | 56.3, 78.8, 86.7 | 42.5, 85.0, 90.0 | 60.0, 63.8, 95.7 |
| 508B0G | 100, 200, 400 | 2.5, 70.0, 75.0 | 57.5, 73.8, 78.4 | 2.5, 80.0, 90.0 | 61.3, 78.8, 95.0 |

TABLE 6b-continued

| Comp. | Glyphosate App. Rate (g a.e./ha) | IPOLA % inhibition (5DAT) | IPOLA % inhibition (11DAT) | IPOLA % inhibition (12DAT) | XANST % inhibition (11DAT) |
|---|---|---|---|---|---|
| 503B5P | 100, 200, 400 | 30.0, 52.5, 75.0 | 41.3, 67.5, 86.0 | 42.5, 70.0, 90.0 | 55.0, 75.0, 82.5 |
| 504A3L | 100, 200, 400 | 31.3, 71.3, 80.0 | 56.3, 67.5, 90.0 | 28.8, 78.8, 91.3 | 57.5, 76.3, 88.8 |
| 504B2I | 100, 200, 400 | 26.3, 43.8, 73.8 | 47.5, 78.8, 90.0 | 41.3, 63.8, 82.5 | 61.3, 78.8, 91.3 |
| 505A6S | 100, 200, 400 | 28.8, 62.5, 80.0 | 58.8, 71.3, 88.4 | 35.0, 75.0, 88.8 | 63.8, 76.3, 81.3 |
| RT Master | 100, 200, 400 | 72.5, 85.0, 85.0 | 63.8, 87.5, 93.4 | 77.5, 96.3, 98.0 | 70.0, 76.3, 92.0 |
| STD2 | 100, 200, 400 | 36.3, 36.3, 41.3 | 23.8, 62.5, 78.4 | 23.8, 50.0, 67.5 | 45.0, 70.0, 97.5 |

The order of efficacy averaged across application rates for the IPOLA % inhibition averaged over both 5 and 12 days after treatment was RT Master>510A4H>508A1B>510B8V>504A3L>505A6S>506A2T>503B5P>506B9Z>504B2I>508B0G>STD2. The order of efficacy for the XANST % inhibition was RT Master>508A1B>504B2I>506B9Z>504A3L>505A6S>506A2T>508B0G>503B5P>STD2>510A4H>510B8V.

Example 7

The effect of 128A5X and composition 139H2K on zebrina pendula (ZEBPE) plants to determine the appropriate rates for commercial control was tested. Aqueous concentrate compositions were prepared containing the indicated amount of glyphosate salt measured in g a.e./L and excipient ingredients as shown in Table 7a.

TABLE 7a

| Comp. | Gly. | 2,4-D | Cmpnt. 1 | wt % |
|---|---|---|---|---|
| 139H2K | IPA (570) | — | NIS5 | 0.05 |
| 128A5X | MEA (480) | — | CIS6 | 9.6 |

The compositions of Table 7a and comparative composition 128A5X were applied to Zebrina pendula (ZEBPE). Results at 29 days after treatment (29DAT), averaged for all replicates of each treatment, are shown in Table 7b.

TABLE 7b

| Composition | Glyphosate Application Rate (g a.e./ha) | ZEBPE % inhibition (29DAT) |
|---|---|---|
| 139H2K | 1000, 2000, 3000, 4000, 5000, 6000, 7000, 8000 | 53.3, 72.7, 87.0, 84.3, 91.7, 90.0, 89.3, 93.3 |
| 128A5X | 1000, 2000, 3000, 4000, 5000, 6000, 7000, 8000 | 43.3, 45.0, 41.7, 48.3, 72.7, 79.0, 81.7, 85.0 |

From the data, application rates of 2000, 3000, 4000 and 5000 g a.e./ha were used for the next set of experiments on Zebrina pendula (ZEBPE).

Example 8

The effect of glyphosate compositions on Zebrina pendula (ZEBPE) plants was tested. Aqueous concentrate compositions were prepared containing the listed amount of glyphosate salt in g a.e./L and excipient ingredients as shown in Table 8a.

TABLE 8a

| Comp. | Gly. | Cmpnt 1 | wt % | Cmpnt 2 | wt % | Cmpnt 3 | wt % | Compnt 4/5 | wt % |
|---|---|---|---|---|---|---|---|---|---|
| 553I3Z | IPA (360) | CIS8 | 9.6 | NIS6 | 6.4 | NIS7 | 1.0 | OTH7/OTH8 | 1.5/1.0 |
| 239K5X | K (480) | CIS15 | 9.2 | — | — | — | — | — | — |
| 128A5X | MEA (480) | CIS6 | 9.6 | — | — | — | — | — | — |

The compositions of Table 8a and comparative composition 128A5X were applied to Zebrina pendula (ZEBPE). Results at 28 days after treatment (28DAT), averaged for all replicates of each treatment, are shown in Table 8b.

TABLE 8b

| Composition | Glyphosate Application Rate (g a.e./ha) | ZEBPE % inhibition (28DAT) |
|---|---|---|
| 553I3Z | 2000, 3000, 4000, 5000 | 73.8, 89.5, 88.0, 91.3 |
| 239K5X | 2000, 3000, 4000, 5000 | 67.5, 82.8, 86.0, 86.0 |
| 128A5X | 2000, 3000, 4000, 5000 | 82.0, 86.3, 86.5, 88.5 |

The most active composition was 128A5X.

Example 9

The effect of glyphosate compositions on Zebrina pendula (ZEBPE) plants was tested. Aqueous concentrate compositions were prepared containing the listed amount of glyphosate salt in wt % and excipient ingredients as shown in Table 9a.

TABLE 9a

| Comp. | Gly. | Cmpt 1 | wt % | Cmpt 2 | wt % | Cmpt 3 | wt % | Cmpt 4 | wt % |
|---|---|---|---|---|---|---|---|---|---|
| 128A5X | MEA (38.2) | CIS6 | 9.6 | — | — | — | — | — | — |
| 128B1T | MEA (38.2) | CIS6 | 9.6 | OTH3 | 3.82 | — | — | — | — |
| 318A9H | K (36.9) | CIS1 | 7.4 | NIS9 | 4.9 | OTH9 | 6.5 | — | — |
| 318B2V | K (36.9) | CIS1 | 7.4 | NIS9 | 4.9 | OTH9 | 6.5 | OTH3 | 3.7 |
| 265A4C | K (31) | CIS10 | 126 g/L | — | — | — | — | — | — |
| 265B0E | K (31) | CIS10 | 126 g/L | OTH3 | 3.1 | — | — | — | — |
| 683A7T | Amm (68) | CIS1 | 9.5 | NIS8 | 11.6 | OTH4 | 0.4 | OTH18 | 0.1 |

The compositions of Table 9a and comparative composition 128A5X were applied to *Zebrina pendula* (ZEBPE). Results at 27 days after treatment (27DAT), averaged for all replicates of each treatment, are shown in Table 9b.

TABLE 9b

| Composition | Glyphosate Application Rate (g a.e./ha) | ZEBPE % inhibition (27DAT) |
|---|---|---|
| 128M1T | 2000, 3500, 5000, 6500 | 70.5, 82.8, 84.3, 91.3 |
| 318A9H | 2000, 3500, 5000, 6500 | 73.0, 75.0, 82.8, 92.3 |
| 318B2V | 2000, 3500, 5000, 6500 | 78.3, 79.3, 83.8, 88.5 |
| 265A4C | 2000, 3500, 5000, 6500 | 81.8, 85.5, 84.3, 93.5 |
| 265B0E | 2000, 3500, 5000, 6500 | 67.5, 75.0, 75.5, 77.5 |
| 683A7T | 2000, 3500, 5000, 6500 | 76.3, 83.8, 84.0, 90.8 |
| 128A5X | 2000, 3500, 5000, 6500 | 73.5, 82.5, 84.3, 87.0 |

The most active composition was 265A4C. 265B0E showed lower rates of control with added oxalic acid. There were compatibility problems between oxalic acid and the other ingredients in 265B0E and 318B2V.

Example 10

The effect of glyphosate compositions on *Commelina benghalensis* (COMBE) plants was tested. Aqueous concentrate compositions were prepared containing the listed amount of glyphosate salt in wt % and excipient ingredients as shown in Table 10a.

TABLE 10a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 128A5X | MEA (38.2) | CIS11 | 9.6 | — | — | — | — | OTH18 | 0.1 |
| 633F3J | Amm (68) | CIS3 | 9.5 | NIS3 | 11.6 | OTH17 | 0.4 | OTH18 | 0.1 |
| 483H8Q | Amm (68) | CIS11 | 5.7 | NIS1 | 8.0 | OTH1 | 8.3 | OTH4/ OTH5 | 0.4/ 0.1 |
| 050A6B | K (30) | CIS12 | 0.8 | — | — | — | — | — | — |

The compositions of Table 10a and comparative composition 128A5X were applied to *Commelina* (COMBE). Results at 33 days after treatment (33DAT), averaged for all replicates of each treatment, are shown in Table 10b.

TABLE 10b

| Composition | Glyphosate Application Rate (g a.e./ha) | COMBE % inhibition (33DAT) |
|---|---|---|
| 128A5X | 600, 800, 1000, 1200 | 34.0, 50.0, 58.0, 63.0 |
| 633F3J | 600, 800, 1000, 1200 | 29.0, 59.0, 62.0, 59.0 |
| 483H8Q | 600, 800, 1000, 1200 | 27.0, 48.0, 52.0, 56.0 |
| 050A6B | 600, 800, 1000, 1200 | 54.0, 65.0, 68.0, 72.0 |

The most active composition was 050A6B.

Example 11

The effect of glyphosate compositions on *Commelina benghalensis* (COMBE) plants was tested. Aqueous concentrate compositions were prepared containing the listed amount of glyphosate salt in wt % and excipient ingredients as shown in Table 11a.

TABLE 11a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 128A5X | MEA (38.2) | CIS 6 | 9.6 | — | | — | — | — | — |
| 483H8Q | Amm (68) | CIS 11 | 5.7 | NIS1 | 8.0 | OTH1 | 8.3 | OTH4/ | 0.4/ |
| | | | | | | | | OTH5 | 0.1 |
| 633F3J | Amm (68) | CIS 11 | 9.5 | NIS3 | 11.6 | OTH4 | 0.4 | OTH5 | 0.1 |
| 634T9P | Amm (65) | CIS1 | 11.0 | NIS8 | 13.4 | OTH4 | 0.4 | OTH5 | 0.1 |
| 765K4S | K (36.3) | CIS5 | 9.0 | NIS4 | 4.0 | CIS7 | 1.0 | — | — |

The compositions of Table 11a and comparative composition 128A5X were applied to *Commelina* (COMBE). Results at 20 days after treatment (20DAT), averaged for all replicates of each treatment, are shown in Table 11b.

TABLE 11b

| Composition | Glyphosate Application Rate (g a.e./ha) | COMBE % inhibition (20DAT) |
|---|---|---|
| 128A5X | 800, 1100, 1400, 1700 | 60.0, 75.0, 65.0, 83.8 |
| 483H8Q | 800, 1100, 1400, 1700 | 26.3, 61.3, 53.8, 72.5 |
| 633F3J | 800, 1100, 1400, 1700 | 35.0, 61.3, 72.5, 72.5 |
| 634T9P | 800, 1100, 1400, 1700 | 41.3, 70.0, 80.0, 81.3 |
| 765K4S | 800, 1100, 1400, 1700 | 52.5, 75.0, 74.3, 79.5 |

The most active composition was 128A5X.

Example 12

The effect of glyphosate compositions on *Commelina benghalensis* (COMBE) plants was tested. Aqueous concentrate compositions were prepared containing the listed amount of glyphosate salt in wt % and excipient ingredients as shown in Table 12a.

TABLE 12a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 128A5X | MEA (38.2) | CIS6 | 9.6 | — | | — | — | — | — |
| 553I3Z | IPA (360) | CIS8 | 9.6 | NIS6 | 6.4 | NIS7 | 1.0 | OTH7/ | 1.5/ |
| | | | | | | | | OTH8 | 1.0 |
| 483H8Q | Amm (68) | CIS 11 | 5.7 | NIS1 | 8.0 | OTH1 | 8.3 | OTH4/ | 0.4/ |
| | | | | | | | | OTH5 | 0.1 |
| 633F3J | Amm (68) | CIS3 | 9.5 | NIS3 | 11.6 | OTH4 | 0.4 | OTH5 | 0.1 |
| 634T9P | Amm (65) | CIS1 | 11.0 | NIS8 | 13.4 | OTH4 | 0.4 | OTH5 | 0.1 |
| 765K4S | K (36.3) | CIS5 | 9.0 | NIS4 | 4.0 | CIS7 | 1.0 | — | — |
| 239K5X | K (480) | CIS 15 | 9.2 | — | | — | — | — | — |

The compositions of Table 12a were applied to *Commelina* (COMBE). Results at 22 days after treatment (22DAT), averaged for all replicates of each treatment, are shown in Table 12b.

TABLE 12b

| Composition | Glyphosate Application Rate (g a.e./ha) | COMBE % inhibition (22DAT) |
|---|---|---|
| 128A5X | 800, 1100, 1400, 1700 | 72.5, 73.3, 83.8, 80.8 |
| 553I3Z | 800, 1100, 1400, 1700 | 75.5, 75.8, 87.2, 88.3 |
| 483H8Q | 800, 1100, 1400, 1700 | 70.0, 75.8, 79.2, 84.2 |
| 633F3J | 800, 1100, 1400, 1700 | 69.2, 74.2, 74.7, 71.7 |
| 634T9P | 800, 1100, 1400, 1700 | 70.8, 74.2, 79.5, 80.0 |
| 765K4S | 800, 1100, 1400, 1700 | 75.0, 70.0, 75.3, 79.2 |
| 239K5X | 800, 1100, 1400, 1700 | 70.5, 77.5, 83.3, 80.0 |

Formulation 553I3Z was the most effective composition for *Commelina*.

Example 13

The effect of glyphosate compositions on *Commelina benghalensis* (COMBE) plants was tested. Aqueous concentrate compositions were prepared containing the listed amount of glyphosate salt in wt % and excipient ingredients as shown in Table 13a.

TABLE 13a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 128A5X | MEA (38.2) | CIS6 | 9.6 | — | | — | — | — | — |
| 481Z7Y | K (35.5) | carfentrazone | 0.18 | — | | — | — | — | — |
| 633F3J | Amm (68) | CIS3 | 9.5 | NIS3 | 11.6 | OTH 4 | 0.4 | OTH5 | 0.1 |
| 634T9P | Amm (65) | CIS1 | 11.0 | NIS8 | 13.4 | OTH 4 | 0.4 | OTH5 | 0.1 |
| 765K4S | K (36.3) | CIS5 | 9.0 | NIS4 | 4.0 | CIS7 | 1.0 | — | — |
| 239K5X | K (480) | CIS 15 | 9.2 | — | | — | — | — | — |

The compositions of Table 13a and RT Master were applied to *Commelina* (COMBE). Results at 20 days after treatment (20DAT), averaged for all replicates of each treatment, are shown in Table 13b.

TABLE 13b

| Composition | Glyphosate Application Rate (g a.e./ha) | COMBE % inhibition (20DAT) |
|---|---|---|
| 128A5X | 600, 700, 800, 900, 1000 | 62.5, 69.2, 63.3, 70.5, 68.8 |
| 481Z7Y | 600, 700, 800, 900, 1000 | 79.7, 91.3, 91.7, 90.5, 97.2 |
| 633F3J | 600, 700, 800, 900, 1000 | 49.2, 64.2, 55.8, 61.7, 65.0 |
| 634T9P | 600, 700, 800, 900, 1000 | 57.5, 70.5, 55.0, 68.5, 68.3 |
| 765K4S | 600, 700, 800, 900, 1000 | 64.2, 69.2, 69.2, 77.5, 71.7 |
| 239K5X | 600, 700, 800, 900, 1000 | 65.8, 66.3, 61.7, 81.3, 69.2 |
| RT Master | 600, 700, 800, 900, 1000 | 80.0, 89.2, 91.3, 89.3, 95.8 |

The most active compositions in this example were RT Master and 481Z7Y. These results indicate that a second active ingredient (2,4-D or carfentrazone) increases the activity of the composition against *Commelina*.

Example 14

The effect of glyphosate compositions on *Commelina benghalensis* (COMBE) plants was tested. Aqueous concentrate compositions were prepared containing the listed amount of glyphosate salt in wt % and excipient ingredients as shown in Table 14a, as well as those shown in Table 13a.

TABLE 14a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 483H8Q | Amm (68) | CIS 11 | 5.7 | NIS1 | 8.0 | OTH1 | 8.3 | OTH4/OTH5 | 0.4/0.1 |
| 770X1C | K (36.7) | CIS5 | 7.0 | NIS10 | 4.0 | CIS4 | 3.0 | — | — |
| 772N5D | K (36.7) | CIS5 | 7.0 | NIS11 | 3.0 | CIS4 | 3.0 | — | — |
| 780Y4O | K (40) | CIS6 | 8.0 | NIS2 | 3.0 | OTH3 | 1.0 | OTH2 | 1.0 |
| 822B9T | K (30.5) | 2,4-D | 1.0 | CIS6 | 6.0 | NIS2 | 2.5 | — | — |
| 822C6U | IPA (36) | 2,4-D | 1.8 | CIS6 | 8.0 | NIS2 | 3.0 | — | — |

The compositions of Tables 13a and 14a and RT Master were applied to *Commelina* (COMBE). Results at 10 days after treatment (10DAT), 24 days after treatment (24DAT) and 41 days after treatment (41 DAT), averaged for all replicates of each treatment, are shown in Table 14b.

TABLE 14b

| Composition | Glyphosate Application Rate (g a.e./ha) | COMBE % inhibition (10DAT) | COMBE % inhibition (24DAT) | COMBE % inhibition (41DAT) |
|---|---|---|---|---|
| 128A5X | 800, 1100, 1400, 1700, 2000 | 1.5, 1.7, 5.2, 6.0, 6.0 | 41.7, 46.7, 53.3, 44.2, 55.0 | 77.2, 96.7, 94.5, 93.0, 92.0 |
| 481Z7Y | 800, 1100, 1400, 1700, 2000 | 84.2, 92.5, 92.5, 93.3, 96.1 | 80.8, 89.3, 91.7, 91.8, 92.7 | 15.0, 26.5, 35.0, 75.5, 62.6 |
| 633F3J | 800, 1100, 1400, 1700, 2000 | 3.0, 1.7, 2.3, 2.3, 5.2 | 20.0, 22.5, 35.0, 34.2, 45.0 | 51.2, 74.2, 74.7, 77.7, 89.7 |
| 634T9P | 800, 1100, 1400, 1700, 2000 | 1.5, 1.7, 5, 4.3, 7.3 | 18.3, 21.7, 35.8, 33.3, 47.9 | 50, 91.7, 94.2, 82.3, 94.6 |
| 765K4S | 800, 1100, 1400, 1700, 2000 | 3.7, 3.0, 1.3, 3.0, 6.1 | 17.5, 38.3, 30.0, 35.0, 43.9 | 62.5, 90.5, 95.0, 96.0, 97.2 |
| 483H8Q | 800, 1100, 1400, 1700, 2000 | 3.7, 1.7, 4.5, 1.2, 4.3 | 26.7, 19.2, 31.7, 24.2, 31.9 | 51.7, 73.0, 89.5, 90.5, 96.0 |
| 770X1C | 800, 1100, 1400, 1700, 2000 | 0.5, 2.3, 2.8, 3.7, 7.1 | 21.7, 24.2, 37.5, 35.0, 44.9 | 55.8, 81.7, 90.5, 99.2, 100.6 |
| 772N5D | 800, 1100, 1400, 1700, 2000 | 2.2, 1.7, 1.5, 3.8, 3.8 | 29.2, 50.8, 36.7, 39.2, 49.2 | 73.5, 86.8, 92.5, 95.5, 96.8 |
| 780Y4O | 800, 1100, 1400, 1700, 2000 | 2.0, 3.0, 1.7, 3.7, 5.0 | 18.3, 31.7, 45.8, 35.0, 44.2 | 54.2, 88.3, 96.3, 90.8, 95.8 |
| 822B9T | 800, 1100, 1400, 1700, 2000 | 34.2, 39.2, 36.7, 39.2, 40.0 | 70.8, 81.7, 79.7, 80.3, 84.7 | 98.3, 97.8, 100.0, 100.0, 100.0 |
| 822C6U | 800, 1100, 1400, 1700, 2000 | 39.2, 42.5, 40.8, 41.7, 42.1 | 78.7, 85.0, 80.0, 91.8, 96.5 | 100.0, 100.0, 100.0, 100.0, 100.0 |
| RT Master | 800, 1100, 1400, 1700, 2000 | 40.0, 41.7, 41.7, 39.2, 38.3 | 77.7, 86.7, 90.7, 90.0, 91.5 | 100.0, 99.7, 100.0, 100.0, 100.0 |

In this experiment, the compositions that were most effective, particularly against *Commelina* regrowth, were 822B9T, 822C6U and RT Master, which all contain 2,4-D as a second active ingredient.

Example 15

The effect of glyphosate compositions on *Commelina benghalensis* (COMBE) plants was tested. Aqueous concentrate compositions were prepared containing the listed amount of glyphosate salt in wt % and excipient ingredients as shown in Table 15a.

TABLE 15a

| Comp. | Gly. | Cmpt 1 | wt % | Cmpt 2 | wt % | Cmpt 3 | wt % | Cmpt 4/5 | wt % |
|---|---|---|---|---|---|---|---|---|---|
| 128A5X | MEA (38.2) | CIS6 | 9.6 | — | | — | — | — | — |
| 822B9T | K (30.5) | 2,4-D | 1.0 | CIS6 | 6.0 | NIS2 | 2.5 | — | |
| 822C6U | IPA (36) | 2,4-D | 1.8 | CIS6 | 8.0 | NIS2 | 3.0 | — | |

The compositions of Table 15a, Ultra Blazer, Cobra and RT Master were applied to *Commelina* (COMBE). Results at 7 days after treatment (7DAT) and 24 days after treatment (24DAT), averaged for all replicates of each treatment, are shown in Table 15b.

TABLE 15b

| Composition | Glyphosate Application Rate (g a.e./ha) | COMBE % inhibition (7DAT) | COMBE % inhibition (24DAT) |
|---|---|---|---|
| 128A5X | 100, 200, 300, 400 | 0.2, 0.2, 0.5, 3.7 | 29.2, 30.8, 28.3, 33.3 |
| 822B9T | 100, 200, 300, 400 | 42.5, 40.0, 43.3, 43.3 | 49.2, 56.7, 72.5, 74.2 |
| 822C6U | 100, 200, 300, 400 | 40.8, 44.2, 45.0, 46.7 | 63.3, 76.7, 79.2, 83.3 |
| Ultra Blazer | 18, 35, 70, 140, 280, 420 | 0.0, 1.7, 4.3, 4.3, 6.7, 8.3 | 10.0, 10.0, 10.8, 15.0, 41.7, 45.0 |
| Cobra | 9, 18, 35, 70, 140, 210 | 7.5, 8.3, 13.3, 13.3, 20.0, 21.7 | 33.3, 46.7, 41.7, 42.5, 44.2, 47.5 |
| RT Master | 100, 200, 300 | 42.5, 41.7, 49.2 | 73.3, 78.3, 82.5 |

This experiment shows that mixtures of glyphosate and 2,4-D, such as 822B9T, 822C6U and RT Master are more efficacious against *Commelina* than single ingredient formulations.

Example 16

The effect of glyphosate compositions on *Commelina benghalensis* (COMBE) plants was tested. Aqueous concentrate compositions were prepared containing the listed amount of glyphosate salt in wt % and excipient ingredients as shown in Table 16a.

TABLE 16a

| Comp. | Gly. | 2,4-D | Cmpnt. 1 | wt % | Cmpnt. 2 | wt % | Cmpnt. 3 | wt % |
|---|---|---|---|---|---|---|---|---|
| 085Z5F | IPA (30.5) | — | CIS9 | 7.5 | — | | — | — |
| 714V9J | IPA (30.4) | — | 2,4-DB | 3.3 | — | | — | — |

The compositions of Table 16a, Assure II and RT Master were applied to *Commelina* (COMBE). Results at 7 days after treatment (7DAT) and 31 days after treatment (31 DAT), averaged for all replicates of each treatment, are shown in Table 16b.

TABLE 16b

| Composition | Glyphosate Application Rate (g a.e./ha) | COMBE % inhibition (7DAT) | COMBE % inhibition (31DAT) |
|---|---|---|---|
| 085Z5F | 300, 400, 500, 600, 700, 800, 900, 1000, 1100, 1200 | 6.0, 5.0, 5.0, 8.0, 9.0, 11.0, 12.0, 16.0, 24.0, 26.0 | 9.0, 22.0, 24.0, 36.0, 46.0, 51.0, 53.0, 57.0, 56.0, 49.0 |
| 714V9J | 300, 400, 500, 600, 700, 800, 900, 1000, 1100, 1200 | 41.0, 44.0, 46.0, 50.0, 53.0, 53.0, 53.0, 58.0, 60.0, 62.0 | 2.0, 20.0, 23.0, 59.0, 54.0, 79.0, 80.0, 78.0, 74.0, 85.0 |
| Assure II | 5, 10, 20, 30, 40, 80, 160 | 9.0, 10.0, 15.0, 12.0, 15.0, 13.0, 19.0 | 5.0, 5.0, 5.0, 5.0, 5.0, 0.0, 0.0 |
| RT Master | 300, 400, 500, 600, 700, 800, 900, 1000, 1100, 1200 | 63.0, 61.0, 70.0, 66.0, 68.0, 74.0, 77.0, 80.0, 80.0, 80.0 | 18.0, 24.0, 64.0, 85.0, 72.0, 94.0, 100.0, 95.0, 96.0, 100.0 |

Both 714V9J and RT Master were effective against *Commelina* in this experiment, however, RT Master was the most efficacious.

Example 17

The effect of glyphosate compositions on morningglory (IPOSS) plants was tested. Aqueous concentrate compositions were prepared containing the listed amount of glyphosate salt in wt % and excipient ingredients as shown in Table 17a.

TABLE 17a

| Comp. | Gly. | 2,4-D | Cmpnt. 1 | wt % | Cmpnt. 2 | wt % | Cmpnt. 3 | wt % |
|---|---|---|---|---|---|---|---|---|
| 085Z5F | IPA (30.5) | — | CIS9 | 7.5 | — | — | — | — |
| 714V9J | (30.4) | — | 2,4-DB | 3.3 | — | — | — | — |

The compositions of Table 17a and RT Master were applied to morningglory (IPOSS). Results at 7 days after treatment (7DAT) and 15 days after treatment (15DAT), averaged for all replicates of each treatment, are shown in Table 17b.

TABLE 17b

| Composition | Glyphosate Application Rate (g a.e./ha) | IPOSS % inhibition (7DAT) | IPOSS % inhibition (15DAT) |
|---|---|---|---|
| 085Z5F | 100, 150, 200, 250, 300, 350, 400, 450, 500, 550, 600, 650, 700 | 12.0, 50.0, 43.0, 50.0, 48.0, 48.0, 51.0, 50.0, 49.0, 52.0, 59.0, 54.0, 60.0 | 8.0, 53.0, 58.0, 63.0, 76.6, 76.0, 79.0, 81.2, 82.8, 80.6, 84.2, 83.2, 84.2 |
| 714V9J | 100, 150, 200, 250, 300, 350, 400, 450, 500, 550, 600, 650, 700 | 17.0, 31.0, 43.0, 39.0, 78.0, 77.0, 66.0, 77.0, 66.0, 77.0, 76.0, 75.0, 82.0, 77.0, 78.0 | 8.0, 20.0, 23.0, 27.0, 30.0, 26.0, 29.0, 34.0, 30.0, 29.0, 30.0, 33.0, 34.0 |
| RT Master | 100, 150, 200, 250, 300, 350, 400, 450, 500, 550, 600, 650, 700 | 54.0, 62.0, 66.0, 70.0, 70.0, 75.0, 76.0, 79.0, 80.0, 84.0, 80.0, 83.0, 81.0 | 42.0, 68.0, 96.0, 97.0, 96.0, 100.0, 100.0, 100.0, 100.0, 100.0, 100.0, 100.0, 100.0 |

RT Master was the most effective composition for controlling morningglory at 7 and 15 days after treatment.

Example 18

The effect of glyphosate compositions on morningglory (IPOSS) plants was tested. Aqueous concentrate compositions were prepared containing the listed amount of glyphosate salt in wt % and excipient ingredients as shown in Table 18a.

TABLE 18a

| Comp. | Gly. | 2,4-D | Cmpnt. 1 | wt % | Cmpnt. 2 | wt % | Cmpnt. 3 | wt % |
|---|---|---|---|---|---|---|---|---|
| 085Z5F | IPA (30.5) | — | CIS9 | 7.5 | — | — | — | — |
| 714V9J | (30.4) | — | 2,4-DB | 3.3 | — | — | — | — |

The compositions of Table 18a, Pursuit and RT Master were applied to morningglory (IPOSS). Results at 14 days after treatment (14DAT), averaged for all replicates of each treatment, are shown in Table 18b.

TABLE 18b

| Composition | Glyphosate Application Rate (g a.e./ha) | IPOSS % inhibition (14DAT) |
|---|---|---|
| 085Z5F | 100, 125, 150, 175, 200, 225, 250, 275, 300, 325, 350, 375, 400 | 7.0, 11.0, 32.0, 44.0, 53.0, 53.0, 55.0, 61.0, 61.0, 61.0, 63.0, 68.0, 76.0 |
| 714V9J | 100, 125, 150, 175, 200, 225, 250, 275, | 6.0, 29.0, 36.0, 31.0, 51.0, 49.0, 68.0, 74.0, |

TABLE 18b-continued

| Composition | Glyphosate Application Rate (g a.e./ha) | IPOSS % inhibition (14DAT) |
|---|---|---|
| | 300, 325, 350, 375, 400 | 66.0, 80.0, 77.0, 74.0, 79.0 |
| Pursuit | 4, 8, 16, 35, 70, 105 | 0.0, 6.0, 36.0, 41.0, 77.0, 80.0 |
| RT Master | 100, 125, 150, 175, 200, 225, 250, 275, 300, 325, 350, 375, 400 | 47.0, 53.0, 66.0, 69.0, 82.0, 75.0, 89.0, 90.0, 78.0, 89.0, 82.0, 89.0, 94.0 |

RT Master was the most efficacious composition at the application levels of the experiment.

Example 19

Aqueous compositions were prepared containing potassium glyphosate salt, IPA 2,4-D salt and excipient ingredients as shown in Table 19a. The formulations were prepared by mixing the 40.5% w/w a.e. aqueous solution of IPA 2,4-D to a concentration in w/w % as indicated by [2,4-D] in Table 19a, surfactant(s), glycol followed by addition of 47.8 (47.4) % w/w a.e. aqueous solution of potassium glyphosate to a concentration in w/w % as indicated by [gly] in Table 19a and then taking the total volume to 100% with water. Formulations were tested for cloud point and for density.

TABLE 19a

| Comp. | [Gly] | [2,4-D] | Cmpt. 1 | wt % | Cmpt. 2 | wt % | Cmpt. 3 | wt % | Cloudpt. ° C. |
|---|---|---|---|---|---|---|---|---|---|
| 612A7G | 37.2 | 0.76 | CIS6 | 4.72 | NIS2 | 4.59 | OTH2 | 4.01 | 72 |
| 613A9L | 37.3 | 1.08 | CIS6 | 4.74 | NIS2 | 4.60 | OTH2 | 3.99 | 52 |
| 638A1J | 36.5 | 0.73 | CIS6 | 4.63 | CIS14 | 4.57 | — | — | 87 |
| 638B4T | 36.8 | 0.75 | CIS6 | 6.19 | CIS14 | 3.05 | — | — | 72 |
| 639A5Z | 36.6 | 0.75 | CIS6 | 6.95 | CIS14 | 2.30 | — | — | 67 |
| 639B3X | 37.1 | 0.76 | CIS6 | 3.95 | NIS2 | 4.57 | CIS14 | 0.78 | 52 |
| 640B7Q | 36.6 | 0.73 | CIS6 | 9.14 | — | — | — | — | 55 |
| 641A9V | 36.7 | 0.74 | CIS6 | 6.95 | CIS13 | 2.30 | — | — | 68 |
| 641B8D | 37.3 | 0.76 | CIS6 | 4.73 | NIS2 | 3.25 | OTH10 | 5.00 | 57 |
| 645A7S | 36.6 | 0.71 | CIS13 | 8.91 | — | — | — | — | >85 |
| 645B2B | 35.8 | 0.65 | CIS6 | 8.09 | OTH2 | 5.51 | — | — | 56 |
| 645C1I | 34.7 | 0.72 | CIS6 | 8.70 | OTH2 | 6.01 | — | — | 60 |
| 646A8K | 36.6 | 0.72 | CIS6 | 4.58 | CIS13 | 4.57 | OTH2 | 1.43 | >85 |
| 646B3Z | 34.8 | 0.69 | CIS6 | 4.35 | CIS13 | 4.35 | OTH2 | 1.67 | >85 |
| 654B9U | 35.8 | 0.64 | CIS6 | 7.97 | — | — | OTH2 | 5.51 | 56 |
| 656A1T | 36.6 | 0.74 | CIS6 | 6.08 | CIS13 | 3.07 | OTH2 | 2.96 | 71 |
| 656B8Y | 36.6 | 0.73 | CIS6 | 7.33 | CIS13 | 1.83 | OTH2 | 4.18 | 54 |
| 656C3G | 36.6 | 0.73 | CIS6 | 7.31 | CIS13 | 1.83 | OTH2 | 3.17 | 70 |
| 665A2T | 34.3 | 0.69 | CIS6 | 8.53 | OTH2 | 6.01 | — | — | 70 |
| 665B3O | 34.2 | 0.68 | CIS6 | 8.55 | OTH2 | 5.00 | — | — | 73 |
| 667B6Z | 34.2 | 0.68 | CIS2 | 8.54 | OTH2 | 4.99 | — | — | 79 |
| 668A5V | 34.2 | 0.69 | CIS6 | 8.56 | OTH10 | 6.02 | — | — | 71 |
| 669B2O | 36.6 | 0.74 | CIS6 | 7.33 | CIS13 | 1.83 | OTH10 | 3.17 | 58 |
| 669C9X | 36.6 | 0.73 | CIS6 | 7.31 | CIS13 | 1.83 | OTH2 | 2.18 | 60 |
| 670A4F | 36.6 | 0.74 | CIS6 | 7.31 | CIS13 | 1.83 | OTH10 | 2.18 | 61 |
| 670B9G | 36.6 | 0.73 | CIS6 | 7.32 | CIS13 | 1.82 | OTH2 | 1.17 | 62 |
| 670C6L | 36.6 | 0.74 | CIS6 | 7.33 | CIS13 | 1.83 | OTH10 | 1.19 | 63 |
| 682A0M | 36.6 | 0.73 | CIS6 | 6.86 | CIS13 | 2.29 | OTH2 | 0.71 | 71 |
| 682B5V | 36.6 | 0.72 | CIS6 | 6.85 | CIS13 | 2.29 | — | — | 69 |
| 682C7P | 36.6 | 0.73 | CIS6 | 6.10 | CIS13 | 3.05 | — | — | 77 |
| 684A4O | 36.6 | 0.73 | CIS6 | 6.53 | CIS13 | 2.61 | OTH2 | 0.40 | 73 |
| 694A9Y | 36.6 | — | CIS6 | 13.8 | — | — | — | — | — |
| 695A2D | 36.6 | — | CIS6 | 8.12 | CIS13 | 4.07 | — | — | — |
| 697A3U | 36.6 | 0.71 | CIS6 | 6.86 | CIS14 | 2.29 | — | — | 70 |
| 697B5Y | 36.6 | 0.71 | CIS6 | 6.85 | CIS14 | 2.29 | OTH2 | 1.48 | 72 |
| 697C2T | 36.6 | 0.71 | CIS6 | 6.11 | CIS14 | 3.05 | — | — | 76 |
| 698A8R | 36.6 | 0.72 | CIS6 | 6.09 | CIS14 | 3.05 | OTH2 | 3.97 | 74 |
| 312A6E | 36.6 | 0.74 | CIS6 | 4.57 | NIS2 | 4.59 | OTH2 | 4.01 | 72 |
| 313A1V | 36.6 | 1.05 | CIS6 | 4.59 | NIS2 | 4.59 | OTH2 | 3.99 | 52 |
| 316A5G | 36.2 | 0.72 | CIS6 | 4.53 | NIS2 | 4.53 | OTH10 | 4.00 | 66 |
| 316B7Y | 36.2 | 0.72 | CIS6 | 4.53 | NIS2 | 4.53 | OTH10 | 3.00 | 61 |
| 317A0J | 36.2 | 0.72 | CIS6 | 4.53 | NIS2 | 4.53 | OTH10 | 2.02 | 57 |
| 318A4B | 35.8 | 0.72 | CIS6 | 4.47 | NIS2 | 4.50 | OTH10 | 4.02 | 71 |
| 338A2W | 36.6 | 0.73 | CIS6 | 4.57 | CIS14 | 4.58 | — | — | 87 |
| 338B4F | 36.7 | 0.74 | CIS6 | 6.09 | CIS14 | 3.04 | — | — | 72 |
| 339A3Q | 36.6 | 0.74 | CIS6 | 6.84 | CIS14 | 2.29 | — | — | 67 |
| 339B9P | 36.6 | 0.74 | CIS6 | 3.83 | CIS14 | 0.77 | NIS2 | 4.57 | 52 |
| 341A7H | 36.6 | 0.73 | CIS6 | 6.84 | CIS13 | 2.29 | — | — | 68 |
| 341B5Z | 36.6 | 0.74 | CIS6 | 4.57 | NIS2 | 3.24 | OTH10 | 5.00 | 57 |
| 346B6T | 36.6 | 0.73 | CIS6 | 6.10 | NIS2 | 3.05 | OTH10 | 4.99 | 55 |
| 346C8X | 35.8 | 0.72 | CIS6 | 4.48 | CIS14 | 0.74 | NIS2 | 3.72 | 58 |
| 351A9M | 35.8 | 0.73 | CIS6 | 4.49 | NIS2 | 4.50 | OTH10 | 5.00 | 74 |
| 351B2V | 35.8 | 0.72 | CIS6 | 5.96 | NIS2 | 2.99 | OTH10 | 5.02 | 62 |
| 352A6G | 35.8 | 0.72 | CIS6 | 3.73 | CIS13 | 0.75 | NIS2 | 4.50 | 63 |
| 352B4N | 36.6 | 0.74 | CIS6 | 4.48 | CIS4 | 4.49 | OTH10 | 5.01 | >90 |
| 352C5Z | 36.6 | 0.73 | CIS6 | 6.73 | CIS4 | 2.24 | OTH10 | 5.01 | 80 |
| 355A9K | 36.6 | 1.46 | CIS6 | 4.58 | CIS4 | 4.59 | OTH10 | 4.99 | 73 |
| 328D3J | 34.3 | 0.69 | CIS6 | 8.60 | OTH10 | 5.99 | — | — | 72 |
| 331H1K | 35.9 | 0.72 | CIS6 | 4.48 | NIS2 | 4.50 | OTH10 | 4.99 | 74 |
| 074A2E | 35.4 | 0.67 | CIS2 | 6.11 | — | — | — | — | 60 |
| 074B9O | 36.3 | 0.51 | CIS2 | 5.97 | — | — | — | — | 62 |
| 075A3Q | 36.2 | 0.54 | CIS2 | 7.55 | — | — | — | — | 66 |
| 077C5Y | 39.9 | 0.15 | CIS2 | 6.78 | — | — | — | — | 61 |
| 078A8U | 38.8 | 0.33 | CIS6 | 6.11 | OTH18 | 0.28 | — | — | 60 |
| 083A6B | 24.3 | 1.99 | CIS2 | 8.94 | — | — | — | — | 64 |
| 083B0V | 27.8 | 1.47 | CIS2 | 6.10 | — | — | — | — | 57 |
| 084A6G | 41.2 | 0.17 | CIS2 | 5.67 | — | — | — | — | 60 |
| 084B4R | 39.8 | 0.24 | CIS2 | 6.64 | — | — | — | — | 62 |
| 084C2W | 36.2 | 0.57 | CIS6 | 7.25 | — | — | — | — | 63 |
| 085A8I | 28.3 | 1.59 | CIS6 | 9.09 | — | — | — | — | 61 |
| 085B3S | 38.9 | 0.29 | CIS6 | 6.79 | — | — | — | — | 61 |
| 085C6H | 39.2 | 0.25 | CIS6 | 6.60 | — | — | — | — | 60 |
| 096A5F | 39.3 | 0.25 | CIS6 | 6.63 | — | — | — | — | 61 |
| 098B2X | 36.4 | 0.57 | CIS6 | 6.05 | — | — | — | — | 60 |
| 100A6T | 28.2 | 1.62 | CIS2 | 9.25 | — | — | — | — | 77 |
| 100B5G | 28.7 | 1.60 | CIS6 | 9.23 | — | — | — | — | 67 |
| 501A8V | 28.7 | 1.66 | CIS2 | 9.18 | — | — | — | — | 66 |

TABLE 19a-continued

| Comp. | [Gly] | [2,4-D] | Cmpt. 1 | wt % | Cmpt. 2 | wt % | Cmpt. 3 | wt % | Cloudpt. ° C. |
|---|---|---|---|---|---|---|---|---|---|
| 503A3S | 36.1 | 0.64 | CIS2 | 9.09 | — | — | — | — | 64 |
| 503C5A | 35.8 | 0.65 | CIS6 | 9.30 | — | — | — | — | 60 |
| 505A4R | 36.1 | 0.72 | CIS2 | 9.05 | — | — | — | — | 60 |
| 505C7P | 35.9 | 0.75 | CIS2 | 7.40 | — | — | — | — | 61 |
| 506B1V | 36.3 | 0.71 | CIS2 | 7.27 | — | — | — | — | 60 |
| 508B2M | 36.1 | 0.72 | CIS2 | 7.53 | — | — | — | — | 60 |
| 508E9C | 35.9 | 0.66 | CIS2 | 7.70 | — | — | — | — | 58 |
| 509B0K | 36.0 | 0.62 | CIS2 | 7.53 | — | — | — | — | 61 |
| 510B7L | 36.2 | 0.59 | CIS6 | 7.59 | — | — | — | — | 61 |
| 548B1Z | 28.4 | 1.59 | CIS2 | 9.12 | — | — | — | — | 56 |
| 564B0Y | 28.3 | 1.66 | CIS6 | 9.13 | OTH3 | 1.02 | — | — | 64 |
| 569B2W | 28.6 | 2.49 | CIS6 | 7.23 | OTH6 | 1.47 | — | — | 64 |
| 580B6G | 28.3 | 3.09 | CIS6 | 7.60 | OTH6 | 2.55 | OTH13 | 2.27 | 65 |
| 581A8J | 28.4 | 3.21 | CIS6 | 6.87 | OTH6 | 2.58 | OTH13 | 2.27 | 61 |
| 581B3E | 27.9 | 3.15 | CIS6 | 3.88 | OTH6 | 4.81 | OTH13 | 5.14 | >90 |
| 405A8N | 28.8 | 2.69 | CIS6 | 9.61 | OTH6 | 1.49 | — | — | 65 |
| 406B7V | 28.8 | 3.08 | CIS6 | 9.22 | OTH6 | 1.65 | — | — | 57 |

Additional aqueous compositions were prepared containing potassium glyphosate salt, 2,4-D acid and excipient ingredients as shown in Table 19b. The formulations were prepared by mixing the 98% w/w a.e. aqueous solution of 2,4-D acid to a concentration in w/w % as indicated by [2,4-D] in Table 19b, surfactant(s), glycol followed by addition of 47.8 (47.4) % w/w a.e. aqueous solution of potassium glyphosate to a concentration in w/w % as indicated by [gly] in Table 19b and then taking the total volume to 100% with water. Formulations were tested for cloud point and for density.

TABLE 19b

| Comp. | [Gly] | [2,4-D] | Cmpt. 1 | wt % | Cmpt. 2 | wt % | Cmpt. 3 | wt % | Cloudpt. ° C. |
|---|---|---|---|---|---|---|---|---|---|
| 447A6T | 23.2 | 2.64 | CIS12 | 8.44 | — | — | — | — | 58 |
| 448A1Z | 23.6 | 2.75 | CIS5 | 9.83 | — | — | — | — | 64 |
| 448C5G | 24.6 | 2.96 | CIS5 | 10.3 | — | — | — | — | 71 |
| 451A0I | 25.5 | 2.99 | CIS5 | 9.83 | — | — | — | — | 50 |
| 472A2W | 26.2 | 2.04 | CIS5 | 1.72 | CIS12 | 5.16 | — | — | 56 |
| 473B8K | 30.4 | 2.99 | CIS5 | 8.42 | — | — | — | — | 61 |
| 474A3R | 28.1 | 2.70 | CIS5 | 11.5 | — | — | — | — | 56 |
| 489A6H | 28.2 | 2.00 | CIS4 | 9.28 | — | — | — | — | 59 |
| 489B9M | 29.1 | 2.90 | CIS4 | 8.55 | — | — | — | — | 72 |
| 489C5V | 28.3 | 2.97 | CIS4 | 9.05 | — | — | — | — | 74 |
| 489D1Q | 28.3 | 2.95 | CIS4 | 8.99 | — | — | — | — | 74 |
| 009C4N | 29.8 | 3.41 | CIS11 | 8.72 | OTH6 | 4.15 | — | — | 69 |
| 012A7O | 27.9 | 3.09 | CIS11 | 8.96 | OTH6 | 2.13 | — | — | 57 |
| 012B2X | 28.1 | 3.10 | CIS11 | 8.85 | OTH5 | 2.55 | — | — | 65 |
| 013A6K | 28.3 | 3.10 | CIS11 | 9.76 | OTH6 | 2.83 | — | — | 66 |
| 013B6T | 28.4 | 3.12 | CIS11 | 9.27 | OTH6 | 2.76 | — | — | 63 |
| 021B0U | 28.4 | 3.14 | CIS15 | 9.17 | OTH6 | 2.77 | — | — | 62 |
| 026A8V | 26.0 | 2.87 | CIS6 | 8.59 | CIS7 | 2.96 | — | — | 64 |
| 026B9Y | 26.7 | 2.84 | CIS2 | 9.19 | CIS7 | 2.54 | — | — | 65 |
| 028A3Q | 27.1 | 2.95 | CIS6 | 10.4 | CIS7 | 1.83 | — | — | 53 |
| 028B0H | 27.5 | 2.99 | CIS2 | 8.74 | CIS7 | 5.81 | — | — | 53 |
| 029A4L | 26.8 | 3.08 | CIS6 | 11.1 | CIS7 | 4.78 | — | — | 60 |
| 029B3V | 28.0 | 3.08 | CIS2 | 9.55 | CIS7 | 5.81 | — | — | 58 |
| 034A6P | 28.3 | 2.92 | CIS2 | 9.95 | OTH16 | 2.68 | — | — | 58 |
| 034B7Y | 27.9 | 2.94 | CIS2 | 9.16 | OTH16 | 2.68 | — | — | 60 |
| 044A1L | 28.8 | 3.08 | CIS2 | 9.00 | OTH6 | 2.39 | — | — | 67 |
| 044B5T | 28.1 | 3.04 | CIS2 | 9.21 | OTH6 | 2.19 | — | — | 66 |
| 045A0X | 38.2 | 3.09 | CIS2 | 9.28 | OTH6 | 2.24 | — | — | 65 |
| 045B8Q | 28.5 | 3.10 | CIS2 | 9.19 | OTH6 | 2.17 | — | — | 65 |
| 046A2W | 28.8 | 3.10 | CIS2 | 9.13 | OTH6 | 2.24 | OTH14 | 1.15 | 75 |
| 047A6F | 28.1 | 3.09 | CIS6 | 9.09 | OTH6 | 1.51 | OTH14 | 1.87 | 62 |
| 047B7K | 28.4 | 3.13 | CIS2 | 9.21 | OTH6 | 2.16 | — | — | 67 |
| 059A0U | 28.4 | 3.13 | CIS2 | 9.21 | OTH6 | 2.19 | — | — | 65 |
| 066B1V | 26.4 | 2.73 | CIS6 | 7.70 | CIS7 | 4.55 | OTH14 | 8.70 | 60 |
| 071A3P | 32.6 | 0.92 | CIS6 | 7.74 | — | — | — | — | 60 |
| 072A5S | 34.6 | 0.60 | CIS2 | 7.84 | — | — | — | — | 60 |
| 072C9W | 36.6 | 0.51 | CIS2 | 7.69 | — | — | — | — | 62 |
| 073A4G | 34.6 | 0.54 | CIS2 | 5.89 | — | — | — | — | 60 |
| 073B0M | 36.3 | 0.47 | CIS2 | 6.08 | — | — | — | — | 62 |

TABLE 19b-continued

| Comp. | [Gly] | [2,4-D] | Cmpt. 1 | wt % | Cmpt. 2 | wt % | Cmpt. 3 | wt % | Cloudpt. ° C. |
|---|---|---|---|---|---|---|---|---|---|
| 501B2U | 29.0 | 1.70 | CIS2 | 9.23 | — | | — | — | 74 |
| 501C9H | 28.7 | 1.82 | CIS2 | 9.07 | — | | — | — | 64 |
| 502A6G | 33.1 | 1.04 | CIS6 | 9.26 | — | | — | — | 62 |
| 502B1J | 34.7 | 0.78 | CIS2 | 9.26 | — | | — | — | 62 |
| 502C7K | 36.2 | 0.61 | CIS2 | 9.10 | — | | — | — | 61 |
| 503B3L | 36.1 | 0.66 | CIS6 | 9.08 | — | | — | — | 61 |
| 504A8T | 36.1 | 0.65 | CIS6 | 9.08 | — | | — | — | 60 |
| 504B4P | 36.1 | 0.74 | CIS2 | 9.09 | — | | — | — | 61 |
| 505B0X | 36.1 | 0.88 | CIS2 | 7.23 | — | | — | — | 50 |
| 506A4R | 36.1 | 0.30 | CIS2 | 7.24 | — | | — | — | 61 |
| 508A5J | 36.1 | 0.30 | CIS2 | 7.62 | — | | — | — | 60 |
| 508C1P | 36.0 | 0.34 | CIS2 | 7.52 | — | | — | — | 58 |
| 508D2W | 35.7 | 0.31 | CIS6 | 7.50 | — | | — | — | 59 |
| 509A9I | 35.8 | 0.28 | CIS2 | 7.67 | — | | — | — | 60 |
| 510A7Z | 36.3 | 0.26 | CIS6 | 7.53 | — | | — | — | 61 |
| 546A0V | 28.4 | 1.57 | CIS2 | 8.46 | OTH9 | 1.92 | — | — | 60 |
| 548A2D | 28.5 | 1.57 | CIS2 | 9.23 | OTH9 | 2.24 | — | — | 60 |
| 549B3X | 28.5 | 1.45 | CIS2 | 9.19 | OTH9 | 2.22 | — | — | 66 |
| 549C1K | 28.5 | 1.45 | CIS2 | 9.23 | OTH9 | 2.03 | — | — | 71 |
| 551B8D | 28.5 | 1.47 | CIS2 | 9.22 | OTH9 | 2.11 | — | — | 66 |
| 553A7U | 28.2 | 1.44 | CIS2 | 9.60 | OTH9 | 2.87 | — | — | 58 |
| 553B2F | 28.4 | 1.44 | CIS2 | 9.19 | OTH9 | 2.55 | — | — | 63 |
| 564A6Y | 28.4 | 1.60 | CIS6 | 9.21 | OTH3 | 1.00 | — | — | 68 |

Additional aqueous compositions were prepared containing potassium glyphosate salt, octyl amine 2,4-D salt and excipient ingredients as shown in Table 19c. The formulations were prepared by mixing an aqueous solution of 2,4-D octyl amine salt to a concentration in w/w % as indicated by [2,4-D] in Table 19b, surfactant(s), glycol followed by addition of 47.8 (47.4) % w/w a.e. aqueous solution of potassium glyphosate to a concentration in w/w % as indicated by [gly] in Table 19b and then taking the total volume to 100% with water. Formulations were tested for cloud point and for density.

TABLE 19c

| Comp. | [Gly] | [2,4-D] | Cmpt. 1 | wt % | Cmpt. 2 | wt % | Cmpt. 3 | wt % | Cloudpt. ° C. |
|---|---|---|---|---|---|---|---|---|---|
| 009A5T | 31.3 | 3.18 | CIS2 | 9.95 | OTH6 | 5.17 | — | — | 81 |
| 009B9Z | 30.4 | 2.94 | CIS11 | 9.33 | OTH6 | 4.76 | — | — | 71 |

Example 20

The effect of glyphosate and combinations of 2,4-D and glyphosate on Roundup® ready soy was tested at 1 day, 3 days and 7 days after treatment. Aqueous concentrate compositions were prepared containing potassium glyphosate salt, reported in wt. % a.e. and excipient ingredients as shown for formulations in Table 19a above. The formulations were compared to RT Master® and Roundup Weathermax®. The compositions and comparative compositions RT Master® and Roundup Weathermax®, were applied to Roundup® ready soy plants. Results, averaged for all replicates of each treatment, are shown in Table 20a.

TABLE 20a

| Composition | Glyphosate Application Rate (g a.e./ha) | RR Soy % inhibition (1DAT) | RR Soy % inhibition (3DAT) | RR Soy % inhibition (7DAT) |
|---|---|---|---|---|
| 656A1T | 841, 1681, 3362 | 15.0, 19.2, 25.0 | 14.2, 19.2, 30.0 | 12.2, 20.0, 44.2 |
| 665A2T | 841, 1681, 3362 | 10.8, 23.3, 25 | 10.8, 26.7, 31.7 | 10.5, 27.5, 48.3 |
| 667B6Z | 841, 1681, 3362 | 13.3, 18.3, 21.7 | 13.3, 18.3, 23.3 | 11.0, 18.3, 39.2 |
| 668A5V | 841, 1681, 3362 | 15.0, 20.8, 21.7 | 15.8, 23.3, 25.0 | 15.5, 25.0, 47.5 |
| 682A0M | 841, 1681, 3362 | 15.0, 18.3, 29.2 | 15.0, 20.8, 30.8 | 13.3, 20.8, 44.2 |
| 646A8K | 841, 1681, 3362 | 12.5, 15.0, 20.8 | 10.0, 17.5, 25.0 | 12.3, 19.2, 35.0 |
| 694A9Y | 841, 1681, 3362 | 4.7, 7.5, 9.5 | 5.0, 7.0, 15.8 | 5.0, 10.0, 15.8 |
| 695A2D | 841, 1681, 3362 | 1.0, 3.0, 5.0 | 3.0, 3.7, 15.0 | 3.0, 3.7, 13.3 |
| Weathermax | 841, 1681, 3362 | 1.0, 1.7, 3.0 | 1.0, 1.3, 4.3 | 0.7, 3.0, 3.7 |
| RT Master | 841, 1681, 3362 | 23.3, 20.0, 17.5 | 23.3, 23.3, 20.8 | 25.8, 41.7, 56.7 |

Example 21

The effect of glyphosate and combinations of 2,4-D and glyphosate on velvetleaf was tested. Aqueous concentrate compositions were prepared containing potassium glyphosate salt, reported in wt. % a.e. and excipient ingredients as shown for the formulations in Table 19a above. The formulations were compared to RT Master® and Roundup Weathermax®. The compositions comparative compositions RT Master® and Roundup Weathermax®, were applied to velvetleaf (*Abutilon theophrasti*, ABUTH) plants. Results, averaged for all replicates of each treatment, are shown in Table 21a.

TABLE 21a

| Composition | Glyphosate Application Rate (g a.e./ha) | ABUTH % inhibition (14DAT) |
|---|---|---|
| 656A1T | 100, 200, 300, 400 | 14.2, 67.5, 83.8, 87.5 |
| 665A2T | 100, 200, 300, 400 | 36.7, 75.8, 85, 91.7 |
| 667B6Z | 100, 200, 300, 400 | 38.3, 74.2, 84.3, 90.3 |
| 668A5V | 100, 200, 300, 400 | 48.3, 78.3, 87.5, 89.5 |
| 682A0M | 100, 200, 300, 400 | 37.5, 72.5, 83.7, 89.8 |
| 646A8K | 100, 200, 300, 400 | 40.8, 80, 85, 90.3 |
| 694A9Y | 100, 200, 300, 400 | 67.5, 82.5, 90.8, 93.3 |
| 695A2D | 100, 200, 300, 400 | 58.3, 79.2, 88, 90.8 |
| Weathermax | 100, 200, 300, 400 | 35.8, 73.3, 85.8, 90.8 |
| RT Master | 100, 200, 300, 400 | 18.3, 70, 80, 89.2 |

The order of efficacy for ABUTH % inhibition averaged over all application rates was 694A9Y>695A2D>668A5V>646A8K>665A2T>667B6Z>Weathermax>682A0M>RT Master>656A1T.

Example 22

The effect of glyphosate and combinations of 2,4-D and glyphosate on velvetleaf was tested at 16 days after treatment. Aqueous concentrate compositions were prepared containing potassium glyphosate salt, reported in wt. % a.e. and excipient ingredients as shown for formulations in Table 22a. The formulations were compared to RT Master® and Roundup Weathermax®. The 681C4J composition in Table 19a, compositions in Table 22a and comparative compositions RT Master® and Roundup Weathermax®, were applied to velvetleaf (*Abutilon theophrasti*, ABUTH) plants. Results, averaged for all replicates of each treatment, are shown in Table 22b.

TABLE 22a

| Comp. | [Gly] | [2,4-D] | Cmpt. 1 | wt % | Cmpt. 2 | wt % | Cmpt. 3 | wt % |
|---|---|---|---|---|---|---|---|---|
| 937C2V | 40.0 | — | CIS6 | 6.65 | CIS14 | 3.34 | — | — |
| 936D9G | 36.6 | — | CIS6 | 13.6 | — | — | — | — |
| 974B3X | 34.3 | 0.69 | CIS6 | 8.60 | OTH10 | 5.99 | — | — |
| 935A8Z | 35.9 | 0.72 | CIS6 | 4.48 | NIS2 | 6.42 | OTH10 | 4.99 |
| 342B6V | 36.2 | — | CIS6 | 9.05 | NIS2 | 6.52 | — | — |
| 346A4F | 36.6 | — | CIS6 | 13.7 | — | — | — | — |
| 353A1S | 36.6 | — | CIS6 | 9.15 | CIS4 | 4.58 | — | — |

TABLE 22b

| Composition | Glyphosate Application Rate (g a.e./ha) | ABUTH % inhibition (16DAT) |
|---|---|---|
| 937C2V | 100, 200, 300, 400 | 30.8, 70.8, 80.8, 91.2 |
| 936D9G | 100, 200, 300, 400 | 44.2, 77.5, 85.5, 94.3 |
| 974B3X | 100, 200, 300, 400 | 41.7, 70.8, 87.5, 92.3 |
| 935A8Z | 100, 200, 300, 400 | 31.7, 62.5, 81.3, 89.0 |
| 342B6V | 100, 200, 300, 400 | 45.8, 73.3, 90.0, 92.0 |
| 346A4F | 100, 200, 300, 400 | 41.7, 70.0, 84.7, 91.8 |
| 353A1S | 100, 200, 300, 400 | 43.3, 77.5, 91.7, 98.3 |
| 681C4J | 100, 200, 300, 400 | 38.3, 70.8, 83.2, 89.3 |

TABLE 22b-continued

| Composition | Glyphosate Application Rate (g a.e./ha) | ABUTH % inhibition (16DAT) |
|---|---|---|
| Weathermax | 100, 200, 300, 400 | 28.3, 72.5, 80.8, 90.0 |
| RT Master | 100, 200, 300, 400 | 25.0, 65.0, 84.2, 92.2 |

The order of efficacy for ABUTH % inhibition averaged over all application rates was 353A1S>936D9G>342B6V>974B3X>346A4F>681C4J>937C2V>Weathermax>RT Master>935A8Z.

Example 23

The effect of glyphosate and combinations of 2,4-D and glyphosate on velvetleaf was tested at 15 days after treatment. Aqueous concentrate compositions were prepared containing potassium glyphosate salt, reported in wt. % a.e. and excipient ingredients as shown for formulations in Tables 22a. The formulations were compared to RT Master® and Roundup Weathermax®. The 338A2W, 338B4F, 339A3Q, 341A7H, 352C5Z and 355A9K compositions in Table 19a, the 974B3X and 935A8Z compositions in Table 23a and comparative compositions RT Master® and Roundup Weathermax®, were applied to velvetleaf (*Abutilon theophrasti*, ABUTH) plants. Results, averaged for all replicates of each treatment, are shown in Table 23a.

TABLE 23a

| Composition | Glyphosate Application Rate (g a.e./ha) | ABUTH % inhibition (15DAT) |
|---|---|---|
| 338A2W | 100, 200, 300, 400 | 41.7, 74.2, 86.5, 90.5 |
| 338B4F | 100, 200, 300, 400 | 43.3, 74.2, 88.0, 90.2 |
| 339A3Q | 100, 200, 300, 400 | 46.7, 70.8, 89.2, 91.3 |
| 341A7H | 100, 200, 300, 400 | 38.3, 73.3, 87.5, 91.7 |
| 352C5Z | 100, 200, 300, 400 | 50.0, 72.5, 85.8, 90.7 |
| 355A9K | 100, 200, 300, 400 | 45.8, 63.3, 84.7, 89.3 |

TABLE 23a-continued

| Composition | Glyphosate Application Rate (g a.e./ha) | ABUTH % inhibition (15DAT) |
|---|---|---|
| 974B3X | 100, 200, 300, 400 | 52.5, 76.7, 88.8, 94.0 |
| 935A8Z | 100, 200, 300, 400 | 43.3, 65.0, 84.2, 88.2 |
| Weathermax | 100, 200, 300, 400 | 35.0, 67.5, 82.5, 96.2 |
| RT Master | 100, 200, 300, 400 | 32.5, 69.2, 84.5, 94.0 |

The order of efficacy for ABUTH % inhibition averaged over all application rates was 974B3X>352C5Z>339A3Q>338B4F>338A2W>341A7H>355A9K>Weathermax>935A8Z>RT Master.

Example 24

The effect of glyphosate and combinations of 2,4-D and glyphosate on Roundup ready soybean plants was tested at 1 day and 3 days after treatment. Aqueous concentrate compositions were prepared containing potassium glyphosate salt, reported in wt. % a.e. and excipient ingredients as shown for formulations in Tables 22a. The formulations were compared to RT Master® and Roundup Weathermax®. The 681C4J, 342B2H, 342C3A, 346A7C, 353A8Q, 338A2W, 338B4F, 339A3Q, 341A7H, 352C5Z and 355A9K compositions in Table 19a, the 937C2V, 936D9G, 974B3X and 935A8Z compositions in Table 22a and comparative compositions RT Master® and Roundup Weathermax®, were applied to Roundup ready soybean (GLXMG) plants using an Al nozzle. Results, averaged for all replicates of each treatment, are shown in Table 24a.

TABLE 24a

| Composition | Glyphosate Application Rate (g a.e./ha) | RR Soy % injury (1 DAT) | RR Soy % injury (3DAT) |
| --- | --- | --- | --- |
| 681C4J | 841, 1681 | 2.0, 4.0 | 2.8, 6.5 |
| 342B2H | 841, 1681 | 2.8, 10.3 | 5.0, 13.3 |
| 342C3A | 841, 1681 | 1.8, 10.0 | 4.8, 11.3 |
| 346A7C | 841, 1681 | 6.5, 14.0 | 5.0, 14.0 |
| 353A8Q | 841, 1681 | 2.3, 10.8 | 6.0, 12.8 |
| 338A2W | 841, 1681 | 25.0, 26.3 | 31.3, 33.8 |
| 338B4F | 841, 1681 | 23.8, 23.8 | 30.0, 35.0 |
| 339A3Q | 841, 1681 | 27.5, 26.3 | 30.0, 35.0 |
| 341A7H | 841, 1681 | 18.8, 30.0 | 21.3, 38.8 |
| 352C5Z | 841, 1681 | 25.0, 31.3 | 27.5, 36.3 |
| 355A9K | 841, 1681 | 21.3, 26.3 | 20.0, 31.3 |
| 937C2V | 841, 1681 | 2.0, 4.0 | 2.3, 6.8 |
| 936D9G | 841, 1681 | 14.5, 20.0 | 9.3, 22.5 |
| 974B3X | 841, 1681 | 28.8, 32.5 | 33.8, 38.8 |
| 935A8Z | 841, 1681 | 25.0, 23.8 | 23.8, 27.5 |
| Weathermax | 841, 1681 | 2.0, 10.0 | 2.0, 5.0 |
| RT Master | 841, 1681 | 21.3, 18.8 | 22.5, 27.5 |

The order of efficacy for % control in Roundup ready soybeans averaged over all application rates using an Al nozzle was 974B3X>352C5Z>339A3Q>338A2W>338B4F>341A7H>935A8Z>355A9K>RT Master>936D9G>346A7C>342B2H>353A8Q>342C3A>Weathermax>681C4J>937C2V.

Example 25

The experiment in Example 24 was repeated using an TT nozzle to apply the formulations to the Roundup ready soybean plants. Results, averaged for all replicates of each treatment, are shown in Table 25a.

TABLE 25a

| Composition | Glyphosate Application Rate (g a.e./ha) | RR Soy % injury (1DAT) | RR Soy % injury (3DAT) |
| --- | --- | --- | --- |
| 681C4J | 841, 1681 | 1.0, 3.5 | 1.0, 2.8 |
| 342B2H | 841, 1681 | 2.3, 6.0 | 2.0, 6.5 |
| 342C3A | 841, 1681 | 3.0, 5.0 | 1.5, 5.5 |
| 346A7C | 841, 1681 | 2.5, 4.5 | 2.3, 5.3 |
| 353A8Q | 841, 1681 | 2.0, 6.0 | 2.3, 6.8 |
| 338A2W | 841, 1681 | 20.0, 26.3 | 16.3, 28.8 |
| 338B4F | 841, 1681 | 22.5, 26.3 | 15.0, 26.3 |
| 339A3Q | 841, 1681 | 22.5, 22.5 | 20.0, 25.0 |
| 341A7H | 841, 1681 | 20.0, 25.0 | 15.0, 26.3 |
| 352C5Z | 841, 1681 | 26.3, 23.8 | 25.0, 30.0 |
| 355A9K | 841, 1681 | 28.8, 26.3 | 27.5, 31.3 |
| 937C2V | 841, 1681 | 1.8, 3.0 | 1.3, 3.5 |
| 936D9G | 841, 1681 | 3.3, 7.3 | 3.3, 12.0 |
| 974B3X | 841, 1681 | 20.0, 26.3 | 16.3, 28.8 |
| 935A8Z | 841, 1681 | 21.3, 26.3 | 18.8, 27.5 |
| Weathermax | 841, 1681 | 2.0, 4.5 | 2.0, 5.0 |
| RT Master | 841, 1681 | 18.8, 20.0 | 22.5, 27.5 |

The order of efficacy for % control in Roundup ready soybeans averaged over all application rates using a TT nozzle was 355A9K>352C5Z>935A8Z>974B3X>338A2W>338B4F>339A3Q>RT Master>341A7H>936D9G>353A8Q>342B2H>342C3A>346A7C>Weathermax>937C2V>681C4J.

Example 26

Aqueous compositions were prepared containing potassium glyphosate salt, dicamba and excipient ingredients as shown in Table 26a. Formulations were tested for cloud point and for density.

TABLE 26a

| Comp. | [Gly] | [dicamba] | Cmpt. 1 | wt % | Cmpt. 2 | wt % | Cmpt. 3 | wt % | Cloudpt. ° C. |
| --- | --- | --- | --- | --- | --- | --- | --- | --- | --- |
| 561A2J | 39.8 | 0.80 | CIS6 | 6.63 | CIS4 | 3.32 | — | — | 51 |
| 561B5M | 39.8 | 0.79 | CIS6 | 6.40 | CIS4 | 3.56 | — | — | 53 |
| 561C3A | 39.8 | 0.79 | CIS6 | 5.97 | CIS4 | 3.98 | — | — | 56 |
| 561D7Y | 39.8 | 0.79 | CIS6 | 5.62 | CIS4 | 4.33 | — | — | 58 |
| 561E8P | 39.8 | 0.50 | CIS6 | 6.64 | CIS4 | 3.32 | — | — | 66 |

What is claimed is:

1. An herbicidal concentrate composition comprising, in aqueous solution:
   (a) glyphosate, in the form of a salt thereof, in a concentration of at least 175 grams acid equivalent per liter;
   (b) an auxin herbicide component comprising one or more auxin herbicides selected from the group consisting of 2,4-D, dicamba, and agriculturally acceptable salts or esters thereof; and
   (c) a surfactant component comprising one or more surfactants selected from the group consisting of:

(i) quaternary ammonium salts having the formula:

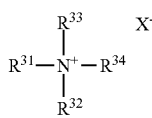 (4)

wherein $R^{31}$ is a linear or branched alkyl or linear or branched alkenyl group having from 8 to 30 carbon atoms, and $R^{32}$, $R^{33}$ and $R^{34}$ are a linear or branched alkyl or linear or branched alkenyl group having from 1 to 30 carbon atoms, and $X^-$ is an agriculturally acceptable anion; and (ii) alkylpolyglycosides having the formula:

 (11)

where $R^{101}$ is hydrogen or $C_{1-18}$ hydrocarbyl, $R^{104}$ is hydrogen or $C_{1-4}$ hydrocarbyl, q is 0 or 1, sug is an open or cyclic structure corresponding to a sugar, u is an average number from 1 to 2, and v is an integer from 1 to 3;

and wherein the composition has a cloud point of at least 50° C.

2. The composition of claim 1 wherein the auxin herbicide component comprises dicamba.

3. The composition of claim 1 wherein the auxin herbicide component comprises 2,4-D.

4. The composition of claim 2 wherein the surfactant component comprises an alkylpolyglycoside having the formula:

 (11)

where $R^{101}$ is hydrogen or $C_{1-18}$ hydrocarbyl, $R^{104}$ is hydrogen or $C_{1-4}$ hydrocarbyl, q is 0 or 1, sug is an open or cyclic structure corresponding to a sugar, u is an average number from 1 to 2, and v is an integer from 1 to 3.

5. The composition of claim 1 wherein the surfactant component comprises a quaternary ammonium salt having the formula:

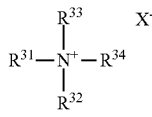 (4)

wherein $R^{31}$ is a linear or branched alkyl or linear or branched alkenyl group having from 8 to 30 carbon atoms, and $R^{32}$, $R^{33}$ and $R^{34}$ are a linear or branched alkyl or linear or branched alkenyl group having from 1 to 30 carbon atoms, and $X^-$ is an agriculturally acceptable anion.

6. The composition of claim 1 comprising glyphosate in the form of the potassium, isopropylamine, di-ammonium, ammonium, sodium, monoethanolamine, n-propylamine, methylamine, ethylamine, hexamethylenediamine, dimethylamine or trimethylsulfonium salt thereof.

7. The composition of claim 6 comprising glyphosate in the form of the potassium, isopropylamine, or monoethanolamine salt thereof.

8. The composition of claim 7 comprising glyphosate in the form of the potassium salt thereof.

9. The composition of claim 8 wherein the composition comprises glyphosate predominantly in the form of the potassium salt thereof.

10. The composition of claim 7 comprising glyphosate in the form of the isopropylamine salt thereof.

11. The composition of claim 10 wherein the composition comprises glyphosate predominantly in the form of the potassium salt thereof.

12. The composition of claim 7 comprising glyphosate in the form of the monoethanolamine salt thereof.

13. The composition of claim 1 wherein the glyphosate is present in an amount of at least 275 grams acid equivalent per liter.

14. The composition of claim 13 wherein the glyphosate is present in an amount of at least 450 grams acid equivalent per liter.

15. The composition of claim 14 wherein the glyphosate is present in an amount of at least 500 grams acid equivalent per liter.

16. The composition of claim 1 wherein total surfactant present in the composition is in an amount of at least 5 wt. % based on the total weight of the composition.

17. The composition of claim 1 wherein the glyphosate (acid equivalent basis) and the surfactant component are present in a weight ratio of from about 2:1 to about 6:1.

18. The composition of claim 1 wherein the composition has a cloud point of at least 60° C.

19. The composition of claim 1 wherein the composition has a crystallization point not higher than 0° C.

20. The composition of claim 1 wherein the composition further comprises an organic solvent, said composition containing not more than 10 weight percent of said organic solvent based on the total weight of the composition.

21. A method of killing or controlling weeds or unwanted vegetation comprising:
diluting the composition of claim 1 an amount of water to form an application mixture; and
applying a herbicidally effective amount of the application mixture to foliage of the weeds or unwanted vegetation.

22. The method of claim 21 wherein the weeds or unwanted vegetation comprise *Commelina*.

* * * * *

UNITED STATES PATENT AND TRADEMARK OFFICE
CERTIFICATE OF CORRECTION

PATENT NO. : 10,499,646 B2  
APPLICATION NO. : 14/273025  
DATED : December 10, 2019  
INVENTOR(S) : David Z. Becher et al.

Page 1 of 1

It is certified that error appears in the above-identified patent and that said Letters Patent is hereby corrected as shown below:

In the Claims

Column 51, Line 28, Claim 4:
"The composition of claim 2 wherein the surfactant"
Should read:
– The composition of claim 1 wherein the surfactant –

Signed and Sealed this  
Seventh Day of July, 2020

Andrei Iancu  
*Director of the United States Patent and Trademark Office*